(12) United States Patent
Dervan et al.

(10) Patent No.: US 10,307,401 B2
(45) Date of Patent: Jun. 4, 2019

(54) COMPOSITIONS AND METHODS FOR TREATMENT OF PROSTATE CANCER

(71) Applicant: California Institute of Technology, Pasadena, CA (US)

(72) Inventors: Peter B. Dervan, San Marino, CA (US); Nickolas G. Nickols, Van Nuys, CA (US); Fei Yang, Pasadena, CA (US); Alexis A. Kurmis, Rochester, NY (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/688,785

(22) Filed: Aug. 28, 2017

(65) Prior Publication Data

US 2018/0064688 A1 Mar. 8, 2018

Related U.S. Application Data

(60) Provisional application No. 62/380,808, filed on Aug. 29, 2016.

(51) Int. Cl.
| | | |
|---|---|---|
| *A61K 31/4178* | (2006.01) | |
| *A61K 31/4166* | (2006.01) | |
| *A61P 35/00* | (2006.01) | |
| *A61P 5/28* | (2006.01) | |
| *A61K 9/00* | (2006.01) | |
| *A61K 45/06* | (2006.01) | |

(52) U.S. Cl.
CPC ........ *A61K 31/4178* (2013.01); *A61K 9/0019* (2013.01); *A61K 31/4166* (2013.01); *A61K 45/06* (2013.01)

(58) Field of Classification Search
CPC ............ A61K 31/4178; A61K 31/4166; A61K 9/0019; C07D 233/66
USPC ................. 514/397; 548/312.4, 314.1, 334.5
See application file for complete search history.

(56) References Cited

U.S. PATENT DOCUMENTS

| | | | |
|---|---|---|---|
| 5,998,140 A | 12/1999 | Dervan | |
| 6,090,947 A | 7/2000 | Dervan | |
| 6,143,901 A | 11/2000 | Dervan | |
| 6,303,312 B1 | 10/2001 | Dervan | |
| 6,472,537 B1 | 10/2002 | Baird | |
| 6,506,906 B1 | 1/2003 | Dervan | |
| 6,545,162 B1 | 4/2003 | Dervan | |
| 6,555,692 B1 | 4/2003 | Dervan | |
| 6,559,125 B1 | 5/2003 | Dervan | |
| 6,635,417 B1 | 10/2003 | Dervan | |
| 6,660,255 B1 | 12/2003 | Gottesfeld | |
| 6,673,940 B1 | 1/2004 | Dervan | |
| 6,958,240 B1 | 10/2005 | Baird | |
| 7,049,061 B1 | 5/2006 | Baird | |
| 7,087,378 B1 | 8/2006 | Baird | |
| 7,452,730 B2 | 11/2008 | Dervan | |
| 7,589,171 B2 | 9/2009 | Bashkin | |
| 9,289,436 B2 | 3/2016 | Szmulewitz | |
| 2003/0109448 A1 | 6/2003 | Crowley | |
| 2005/0026174 A1 | 2/2005 | Dervan | |
| 2006/0014163 A1 | 1/2006 | Dervan | |
| 2006/0019972 A1 | 1/2006 | Dervan | |
| 2006/0025429 A1 | 2/2006 | Dervan | |
| 2006/0270727 A1 | 11/2006 | Melander | |
| 2017/0260169 A1* | 9/2017 | Dervan ............. A61K 31/4178 |

FOREIGN PATENT DOCUMENTS

| | | |
|---|---|---|
| WO | WO 97/30975 | 8/1997 |
| WO | WO 98/35702 | 8/1998 |
| WO | WO 98/37066 | 8/1998 |
| WO | WO 98/37087 | 8/1998 |
| WO | WO 98/45284 | 10/1998 |
| WO | WO 98/49142 | 11/1998 |
| WO | WO 98/50058 | 11/1998 |
| WO | WO 03/041128 | 5/2003 |

OTHER PUBLICATIONS

Ahmed et al., 2014, "Advances in Androgen Receptor Targeted Therapy for Prostate Cancer," J. Cell Physiol. 229(3):1-14.
Almarsson et al., 1993, "Molecular mechanics calculations of the structures of polyamide nucleic acid DNA duplexes and triple helical hybrids," Proc. Natl. Acad. Sci. USA 90:7518-7522.
"Cancer Facts & Figures 2016," American Cancer Society:1-72.
Arora et al., 2013, "Glucocorticoid Receptor Confers Resistance to Antiandrogens by Bypassing Androgen Receptor Blockade," Cell 155:1309-1322.
Asangani et al., 2014, "Therapeutic targeting of BET bromodomain proteins in castration-resistant prostate cancer," Nature 510:278-282.
Baird et al., 1996, "Solid Phase Synthesis of Polyamides Containing Imidazole and Pyrrole Amino Acids," J. Am. Chem. Soc. 118:6141-6146.
Beer et al., 2014, "Enzalutamide in Metastatic Prostate Cancer before Chemotherapy," N. Engl. J. Med. 371(5):424-433.
Beltran et al., 2016, "Divergent clonal evolution of castration-resistant neuroendocrine prostate cancer," Nature Medicine 22(3):298-305.
Best et al., 2003, "Nuclear localization of pyrrole-imidazole polyamide-fluorescein conjugates in cell culture," Proc. Natl. Acad. Sci. USA 100(21):12063-12068.
Burnett et al., 2006, "DNA sequence-specific polyamides alleviate transcription inhibition associated with long GAA•TTC repeats in Friedrich's ataxia," Proc. Natl. Acad. Sci. USA 103(31):11497-11502.
Chen et al., 2004, "Molecular determinants of resistance to antiandrogen therapy," Nature Medicine 10(1):33-39.
Cheng et al., 2006, "Short Hairpin RNA Knockdown of the Androgen Receptor Attenuates Ligand-Independent Activation and Delays Tumor Progressions," Cancer Res. 66(21):10613-10620.

(Continued)

*Primary Examiner* — Irina Neagu

(57) ABSTRACT

The present invention relates to compositions and methods for the treatment of prostate cancer. The present invention relates to polyamides and prostate agents, for example, to inhibit an androgen receptor signaling axis, and the use of these compositions in the treatment of prostate cancer.

9 Claims, 33 Drawing Sheets

(56) References Cited

OTHER PUBLICATIONS

Figure 1:
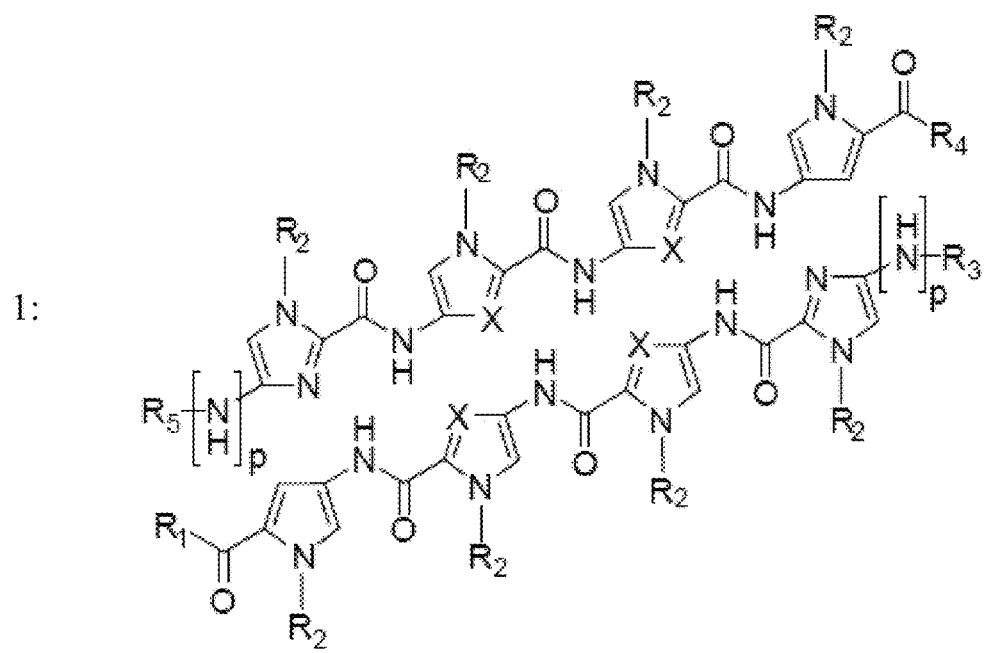

Chenoweth et al., 2009, "Allosteric modulation of DNA by small molecules," Proc. Natl. Acad. Sci. USA 106(32):13175-13179.

Chenoweth et al., 2010, "Structural Basis for Cyclic Py-Im Polyamide Allosteric Inhibition of Nuclear Receptor Binding," J. Am. Chem. Soc. 132:14521-14529.

Cherny et al., 1993, "DNA unwinding upon strand-displacement binding of a thymine-substituted polyamide to double-stranded DNA," Proc. Natl. Acad. Sci. USA 90:1667-1670.

Chiang et al., 2000, "Targeting the Ets Binding Site of the HER2/neu Promoter with Pyrrole-Imidazole Polyamides," J. Biol. Chem. 275(32):24246-24254.

Coull et al., 2002, "Targeted Derepression of the Human Immunodeficiency Virus Type 1 Long Terminal Repeat by Pyrrole-Imidazole Polyamides," J. Virology 76(23):12349-12354.

Dalal et al., 2014, "Selectively Targeting the DNA-binding Domain of the Androgen Receptor as a Prospective Therapy for Prostate Cancer," J. Biol. Chemistry 289(38):26417-26429.

DePrimo et al., 2002, "Transcriptional programs activated by exposure of human prostate cancer cells to androgen," Genome Biology 3(7):research0032.1-0032.12.

Dervan, 2001, "Molecular Recognition of DNA by Small Molecules," Bioorganic & Medicinal Chem. 9:2215-2235.

Dervan et al., 2003, "Recognition of the DNA minor groove by pyrrole-imidazole polyamides," Curr. Opin. Struct. Biol. 13:284-299.

Dickinson et al., 1998, "Inhibition of RNA polymerase II transcription in human cells by synthetic DNA-binding ligands," Proc. Natl. Acad. Sci. USA 95:12890-12895.

Dickinson et al., 2004, "Arresting Cancer Proliferation by Small-Molecule Gene Regulation," Chemistry & Biology 11: 1583-1594.

Dudouet et al., 2003, "Accessibility of Nuclear Chromatin by DNA Binding Polyamides," Chemistry & Biology 10:859-867.

Edelson et al., 2004, "Influence of structural variation on nuclear localization of DNA-binding polyamde-fluorophore conjugates," Nucleic Acids Res. 32(9):2802-2818.

Ehley et al., 2002, "Promoter Scanning for Transcription Inhibition with DNA-Binding Polyamides," Molecular and Cellular Biology 22(6):1723-1733.

Ferraldeschi et al., 2013, "Abiraterone and Novel Antiandrogens: Overcoming Castration Resistance in Prostate Cancer," Annu. Rev. Med. 64:1-13.

Gottesfeld et al., 2001, "Sequence-specific Recognition of DNA in the Nucleosome by Pyrrole-Imidazole Polyamides," J. Mol. Biol. 309:615-629.

Gundem et al., 2015, "The evolutionary history of lethal metastatic prostate cancer," Nature 520:353-357.

Gupta et al., 2002, "Molecular mechanisms of glucocorticoid action," Current Science 83(9):1103-1111.

Gygi et al., 2002, "Use of fluorescent sequence-specific polyamides to discriminate human chromosomes by microscopy and flow cytometry," Nucleic Acids Res. 30(13):2790-2799.

Hargrove et al., 2015, "Tumor Repression of VCaP Xenografts by a Pyrrole-Imidazole Polyamide," PLOS One 10(11):e0143161.

Holzbeierlein et al., "Gene Expression Analysis of Human Prostate Carcinoma during Hormonal Therapy Identifies Androgen-Responsive Genes and Mechanisms of Therapy Resistance," Am. J. of Pathology 164(1):217-227.

Hsu et al., 2007, "Completion of a Programmable DNA-Binding Small Molecule Library," Tetrahedron 63(27):6146-6151.

Hurley, 2002, "DNA and its associated processes as targets for cancer therapy," Nature Reviews 2:188-200.

Isaacs et al., 2004, "Androgen receptor outwits prostate cancer drugs," Nature Medicine 10(1):26-27.

Kelly et al., 1996, "Binding site size limit of the 2:1 pyrrole-imidazole polyamide-DNA motif," Proc. Natl. Acad. Sci. USA 93:6981-6985.

Klein et al., 1997, "Progression of metastatic human prostate cancer to androgen independence in immunodeficient SCID mice," Nature Medicine 3(4):402-408.

Lacy et al., 2002, "Recognition of T•G mismatched base pairs in DNA by stacked imidazole-containing polyamides: surface plasmon resonance and circular dichroism studies," Nucleic Acids Res. 30(8):1834-1841.

Lacy et al., 2004, "Energetic basis for selective recognition of T•G mismatched base pairs in DNA by imidazole-rich polyamides," Nucleic Acids Res. 32(6):2000-2007.

Marques et al., 2002, "Toward an Understanding of the Chemical Etiology for DNA Minor-Groove Recognition by Polyamides," Helvetica Chimica Acta 85:4485-4517.

Massie et al., 2007, "New androgen receptor genomic targets show an interaction with the ETS1 transcription factor," EMBO reports 8(9):871-878.

McGinley et al., 2007, "Circumventing Anti-Androgen Resistance by Molecular Design," J. Am. Chem. Soc.

Meijsing et al., 2009, "DNA Binding Site Sequence Directs Glucocorticoid Receptor Structure and Activity," Science 324:407-410.

Melander et al., 2004, "Regulation of gene expression with pyrrole-imidazole polyamides," J. Biotechnology 112:195-220.

Myung et al., 2013, "An androgen receptor N-terminal domain antagonist for treating prostate cancer," J. Clin. Invest. 123(7):2948-2960.

Neamati et al., 1998, "Highly Potent Synthetic Polyamides, Bisdistamycins, and Lexitropsins as Inhibitors of Human Immunodeficiency Virus Type 1 Integrase," Molecular Pharmacology 54:280-290.

Nelson et al., 2003, "Prostate Cancer," N. Eng. J. Med. 349(4):366-381.

Nickols et al., 2006, "Improved nuclear localization of DNA-binding polyamides," Nucleic Acids Res. 35(2):363-370.

Nickols et al., 2007, "Modulating Hypoxia-Inducible Transcription by Disrupting the HF-1-DNA Interface," ACS Chemical Biology 2(8):561-571.

Nickols et al., 2007, "Suppression of androgen receptor-mediated gene expression by a sequence-specific DNA-binding polyamide," Proc. Natl. Acad. Sci. USA 104(25):10418-10423.

Norgaard et al., 1991, "Glucocorticoid receptors in human malignancies: A review," Annals of Oncology 2:541-557.

O'Hare et al., "DNA sequence recognition in the minor groove by crosslinked polyamides: The effect of N-terminal head group and linker length on binding affinity and specificity," Proc. Natl. Acad. Sci. USA 99(1):72-77.

Olenyuk et al., 2004, "Inhibition of vascular endothelial growth factor with a sequence-specific hypoxia response element antagonist," Proc. Natl. Acad. Sci. USA 101(48):16768-16773.

Philips et al., 2005, "DNA Damage Effects of a Polyamide-CBI Conjugate in SV40 Virions," Mol. Pharmacol. 67:877-882.

Pilch et al., 1996, "Binding of a hairpin polyamide in the minor groove of DNA: Sequence-specific enthalpic discrimination," Proc. Natl. Acad. Sci. USA 93:8306-8311.

Rosen et al., 2005, "The Search for Safer Glucocorticoid Receptor Ligands," Endocrine Reviews 26(3):452-464.

Sazani et al., 2001, "Nuclear antisense effects of neutral, anionic and cationic oligonucleotide analogs," Nucleic Acids Res. 29(19):3965-3974.

Schaal et al., 2003, "Inhibition of human papilloma virus E2 DNA binding protein by covalently linked polyamides," Nucleic Acids Res. 31(4):1282-1291.

Scher et al., 2005, "Biology of Progressive, Castration-Resistant Prostate Cancer: Directed Therapies Targeting the Androgen-Receptor Signaling Axis," J. Clin. Oncol. 23(32):8253-8261.

Sharifi et al., 2006, "Androgen Receptor as a Therapeutic Target for Androgen Independent Prostate Cancer," Am. J. Therapeutics 13:166-170.

Taplin et al., 2008, "A phase II study of mifepristone (RU-486) in castration-resistant prostate cancer, with a correlative assessment of androgen-related hormones," J. Compil. 101:1084-1089.

(56) References Cited

OTHER PUBLICATIONS

Tomlins et al., 2005, "Recurrent Fusion of TMPRSS2 and ETS Transcription Factor Genes in Prostate Cancer," Science 310:644-648.

Tomlins et al., 2006, "TMPRSS2:ETV4 Gene Fusions Define a Third Molecular Subtype of Prostate Cancer," Cancer Res. 66(7):3396-3400.

Trauger et al., 1996, "Extension of Sequence-Specific Recognition in the Minor Groove of DNA by Pyrrole-Imidazole Polyamides to 9-13 Base Pairs," J. Am. Chem. Soc. 118:6160-6166.

Tsai et al., 2006, "Unanticipated differences between α- and γ-diaminobutyric acid-linked hairpin polyamide-alkylator conjugates," Nucleic Acids Res. 35(1):307-316.

Urbach et al., 2001, "Toward rules for 1:1 polyamide:DNA recognition," Proc. Natl. Acad. Sci. USA 98(8):4343-4348.

Urbach et al., 2002, "Structure of a β-Alanine-linked Polyamide Bound to a Full Helical Turn of Purine Tract DNA in the 1:1 Motif," J. Mol. Biol. 320:55-71.

Wang et al., 2003, "DNA crosslinking and biological activity of a hairpin polyamide-chlorambucil conjugate," Nucleic Acids Res. 31(4):1208-1215.

Ware et al., 2014, "Biologic and clinical significance of androgen receptor variants in castration resistant prostate cancer," Endocr. Relat. Cancer 21(4):T87-T103.

Warren et al., 2006, "Defining the sequence-recognition profile of DNA-binding molecules," Proc. Natl. Acad. Sci. USA 103(4):867-872.

Watson et al., 2015, "Emerging mechanisms of resistance to androgen receptor inhibitors in prostate cancer," Nat. Rev. Cancer 15:701-711.

White et al., 1996, "Effects of the A•T/T•A Degeneracy of Pyrrole-Imidazole Polyamide Recognition in the Minor Groove of DNA," Biochemistry 35:12532-12537.

Wurtz et al., 2002, "Inhibition of DNA Binding by NF-κB with Pyrrole-Imidazole Polyamides," Biochemistry 41:7604-7609.

Yang et al., 2013, "Antitumor activity of a pyrrole-imidazole polyamide," Proc. Natl. Acad. Sci. USA 110(5):1863-1868.

Yang et al., 2013, "Animal Toxicity of Hairpin Pyrrole-Imidazole Polyamides Varies with the Turn Unit," J. Med. Chem. 56:7449-7457.

\* cited by examiner

7: 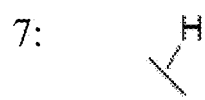 8: 
9:  10: 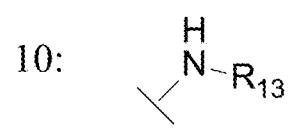
11: 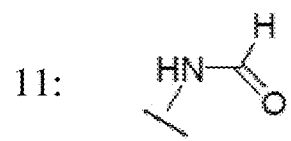 12: 
13: 
14: 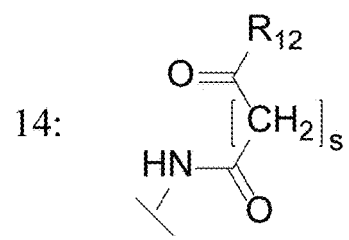 15: 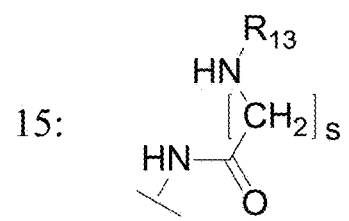
16: 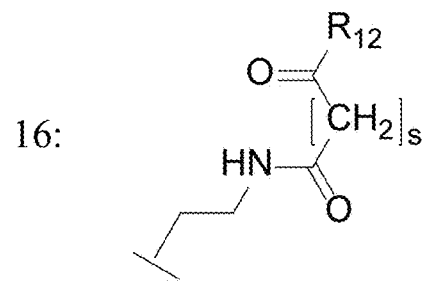 17: 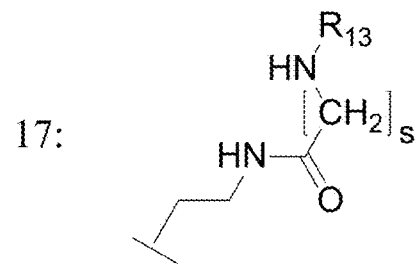
FIG. 3

18: 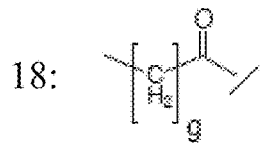  19: 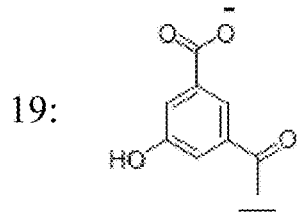
20: 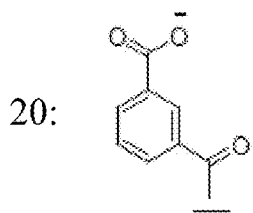  21: 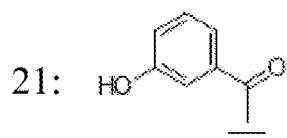
22: 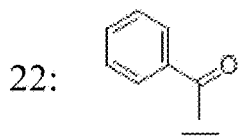  23: 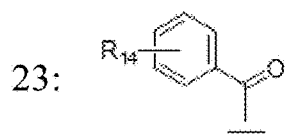
24: 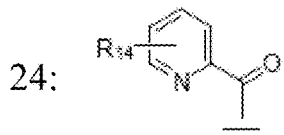  25: 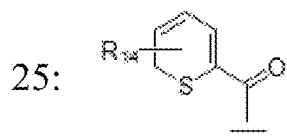
26: 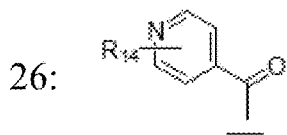  27: 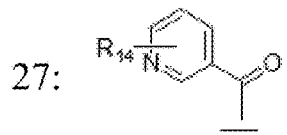
28: 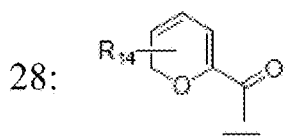  29: 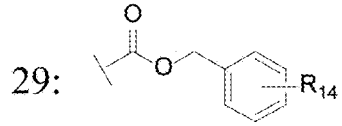
FIG. 4

40: 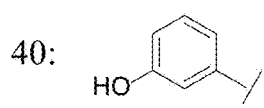  41: 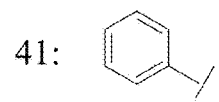
42: 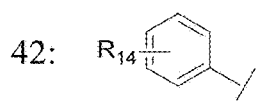  43: 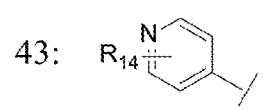
44: 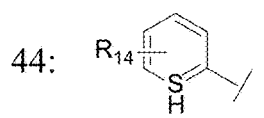  45: 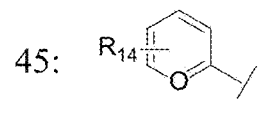
46: 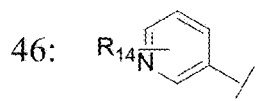  47: 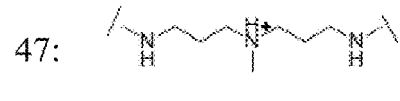
48: 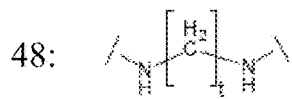  49: 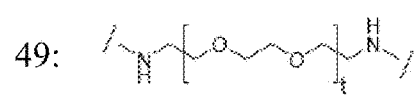
50:   51: 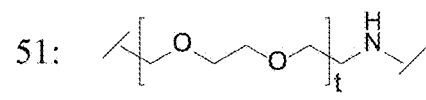
52: 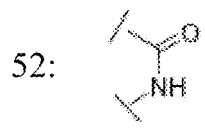  53: 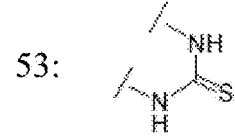
FIG. 5B

Figure 6D:
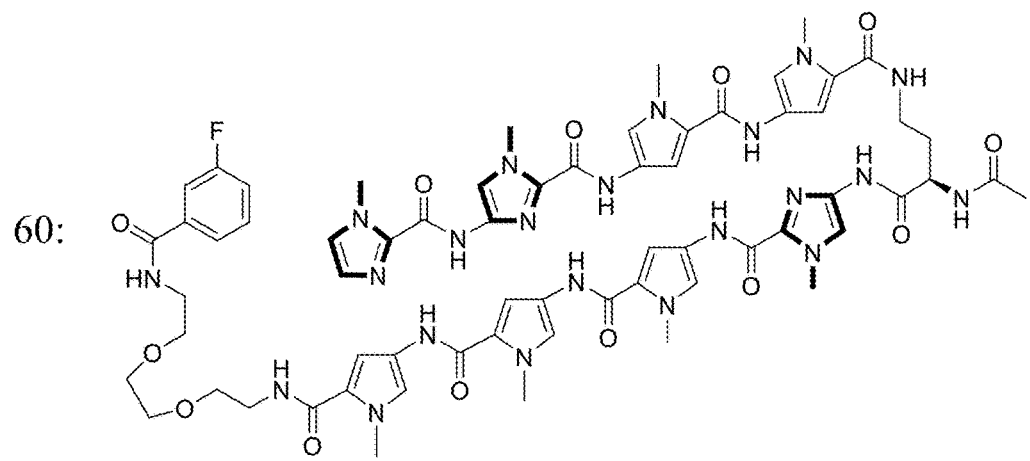

54: 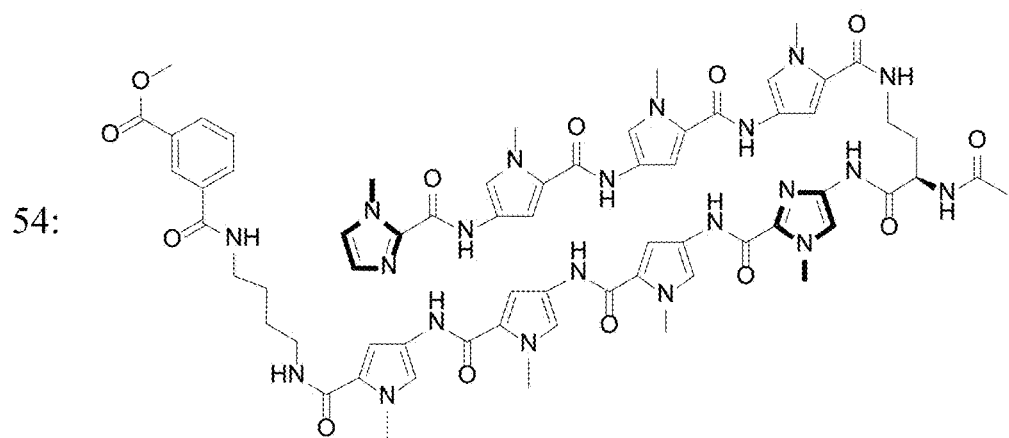
55: 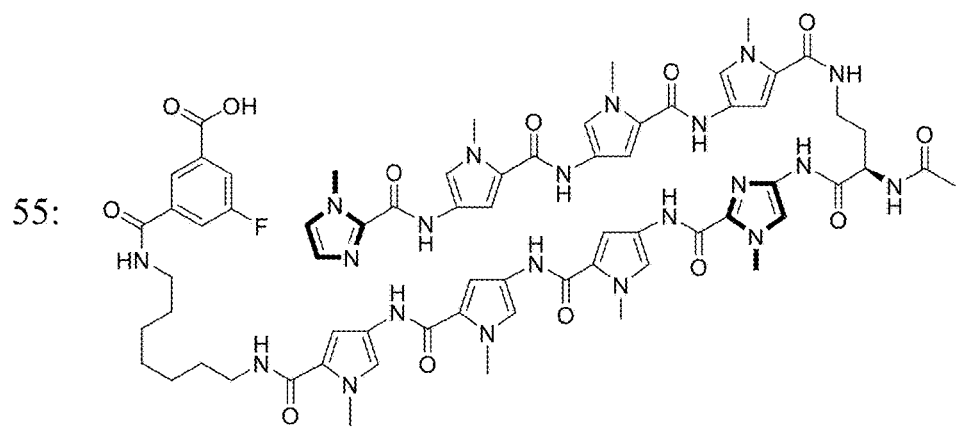
FIG. 6A

56: 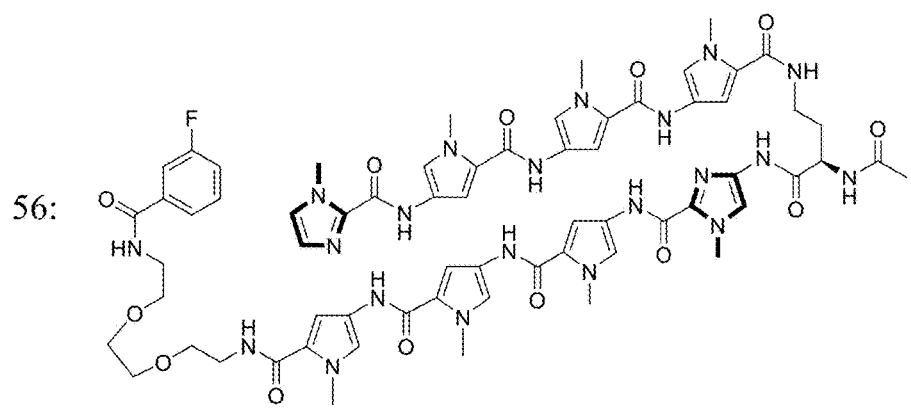
57: 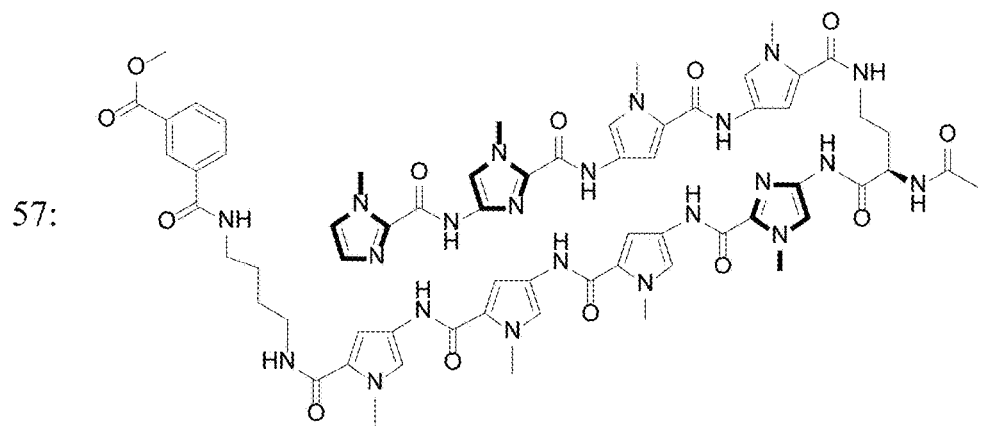
FIG. 6B

58: 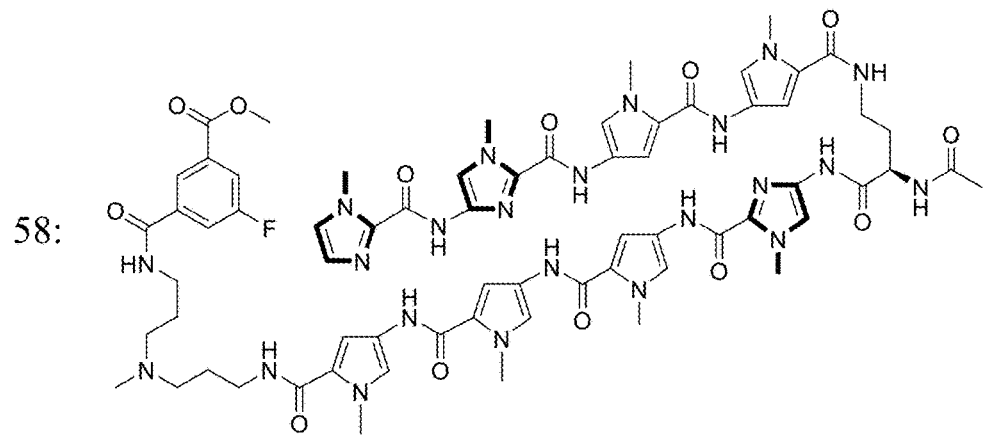
59: 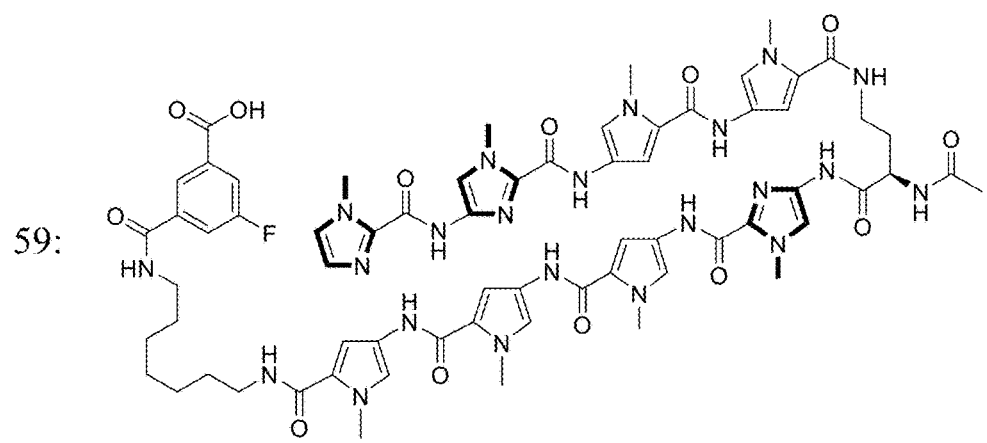
FIG. 6C

60:

A
ARE-1 R = IPA
ARE-1-FITC R = FITC
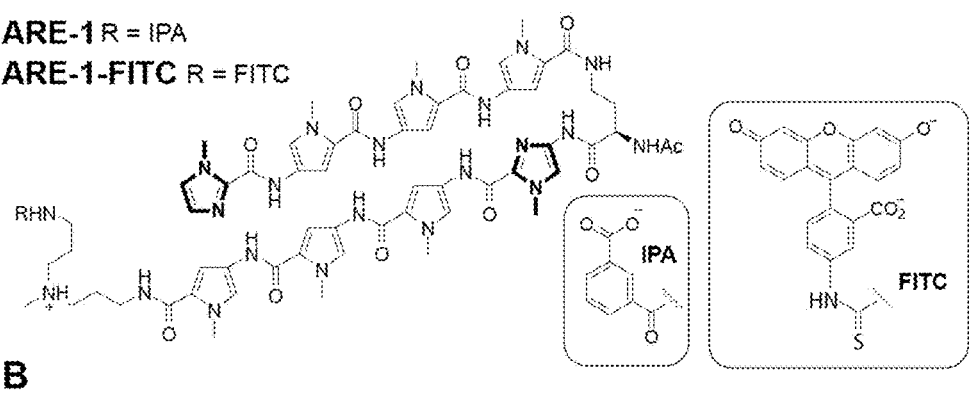
B
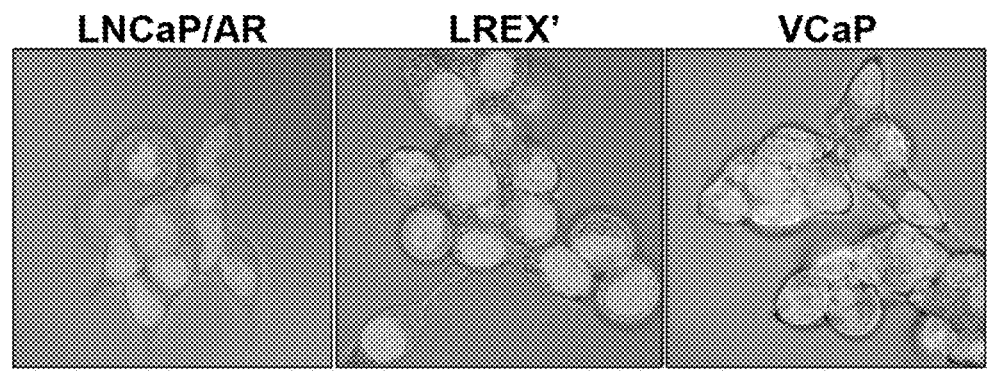
FIG. 8A-B

COMPOSITIONS AND METHODS FOR TREATMENT OF PROSTATE CANCER

This application claims the benefit of U.S. Provisional Application No. 62/380,808, filed Aug. 29, 2016, which is incorporated herein by reference in its entirety.

This invention was made with government support under GM051747 and GM027681 awarded by the National Institutes of Health. The U.S. Government has certain rights in the invention.

1.0 FIELD OF THE INVENTION

The present invention relates to compositions and methods for the treatment of prostate cancer. The present invention relates to polyamides and prostate agents, for example, to inhibit an androgen receptor signaling axis, and the use of these compositions in the treatment of prostate cancer.

2.0 BACKGROUND

Prostate cancer is one of the leading causes of cancer death in men in the world, with over one million new cases diagnosed every year. Many prostate cancer deaths result from a progression of treatment resistant metastatic disease. A treatment for metastatic prostate cancer is androgen deprivation therapy (ADT). ADT interferes with gene transcription mediated by Androgen Receptor (AR) by lowering serum testosterone to castrate levels. A drawback of ADT is the emergence of castration-resistance, often through up-regulation of AR mRNA, which renders AR less sensitive to therapies that directly or indirectly interfere with androgen-AR binding. Therapeutics that inhibit androgen-AR binding include enzalutamide, which is an AR-ligand binding domain antagonist that prevents AR nuclear translocation and improves overall survival in patients with metastatic castrate resistant prostate cancer (CRPC). Yet, many patients develop a form of prostate cancer that is resistant to drugs like enzalutamide.

It would be highly desirable to have therapeutics that are effective in the treatment of prostate cancers, including forms that have developed a resistance of available therapies. The present invention describes such therapeutics.

3.0 SUMMARY OF THE INVENTION

The present invention relates to combination drugs useful for the treatment of prostate cancer and related methods. In certain embodiments, a combination drug of the current invention comprises a polyamide and a prostate agent.

A polyamide of a combination drug of the current invention, in certain embodiments, is capable of modulating androgen receptor (AR)- and glucocorticoid receptor (GR)-mediated gene regulation in a cell. Polyamides of the current invention, in certain embodiments, are capable of entering a cell and of binding to the androgen response element (ARE) and/or the glucocorticoid response element (GRE) in the genome of the cell so as to inhibit binding of nuclear hormone receptors (NHR) to the ARE and/or GRE. Polyamides of the current invention, in certain embodiments, are capable of binding the DNA sequence 5'-WGWWCW-3' and/or 5'-WGGWCW-3' (W=A or T), which is found in a subset of ARE and GRE half-sites.

Polyamides of a combination drug of the current invention, in certain embodiments, comprise a structure 1, wherein each X in structure 1 may be independently selected from a CH, N, CF, COH, or COMe (each p independently selected from 0 and 1), wherein each $R_2$ is independently selected from H, a $C_{1-10}$ alkyl, a $C_{1-10}$ alkenyl, a $C_{1-10}$ alkynyl, —(CH2)$_q$—NH—$R_6$ (each q independently selected from 1-10). Each $R_6$ is independently selected from structures 18-29. Any $R_2$ may be covalently linked to another $R_2$ by a $C_{1-10}$ alkyl, a $C_{1-10}$ alkenyl, or a $C_{1-10}$ alkynyl linker to form an H- or U-shaped molecule. In structure 1, each pyrrole unit of structure 2 may be independently replaced by a beta-alanine of structure 3. Each $R_3$ and $R_4$, and/or each $R_1$ and $R_5$ in structure 1 may be covalently linked by a turn of any one of structures 4-6 to form a hairpin- or a cyclic-shaped molecule. Each $R_1$ and $R_4$ (for example, in structure 1) may also be independently selected from structures 30-37. Each $R_7$, $R_8$, $R_9$, $R_{10}$, and $R_{11}$ in structures 4-6 may be independently selected from an R or S isomer, and is independently selected from OH, OMe, OEt, F, Cl, Br, I, and structures 7-17 (each s independently selected from 1-10). Each $R_{12}$ (for example, in structures 14 and 16) is independently selected from H, OH, OMe, OEt, NH2, NHMe, CH3, and structures 30-37. Each $R_{13}$ (for example, in structures 10, 13, 15, and 17) is independently selected from structures 18-29. Each Y is independently selected from structures 47-51. Each $R_{15}$ (for example, in structure 37) is independently selected from structures 18-29 and 38-46. Each e, g, and t is independently selected from 1-10. Each $R_{14}$ represents one, two, three, four, or five sidechains of the ring (up to the maximum number) with each $R_{14}$ being independently selected from H, OH, OMe, OEt, $CH_3$, $CH_2CH_3$, $NH_2$, F, Cl, Br, I, COOH, COOMe, COOEt, $CONH_2$, CN, NCOMe, $NO_2$, $SO_3$, $PO_4$, and $CH_2PO_3$, and each amide linkage of structure 52 that occurs in structures 35-37 may be independently replaced by a thiourea linkage of structure 53 or the reverse orientation of structure 52. Polyamides of the current invention, in certain preferred embodiments, comprise any one or more of structures 54-61.

A prostate agent of a combination drug of the current invention, in certain embodiments, comprises a hormone therapeutic, an anti-androgen, a cytochrome P17 inhibitor, a taxane, and/or an inhibitor of AR nuclear translocation. In certain embodiments, a hormone therapeutic may comprise histrelin, triptorelin, goserelin, leuprolide (for example, Lupron, Eligard, and/or Leuprolide acetate), and/or degarelix. In certain embodiments, an anti-androgen may comprise flutamide, nilutamide, bicalutamide, enzalutamide, apalutamide, darolutamide, proxalutamide, and/or cyproterone acetate. In certain embodiments, a cytochrome P17 inhibitor may comprise ketoconazole, abiraterone acetate, orteronel, and/or seviteronel. In certain embodiments, a taxane may comprise cabazitaxel, docetaxel, and/or paclitaxel. In certain embodiments, an inhibitor of AR nuclear translocation may comprise enzalutamide, apalutamide, darolutamide, docetaxel, proxalutamide, cabazitaxel, and/or paclitaxel.

The present invention also comprises methods for the treatment of prostate cancer, for example, by administering a combination drug of the current invention to a patient, for example, a human and/or an animal.

4.0 BRIEF DESCRIPTION OF THE DRAWINGS

FIG. 1: Polyamides of certain embodiments of the invention are shown as structure 1.

Figure 2:
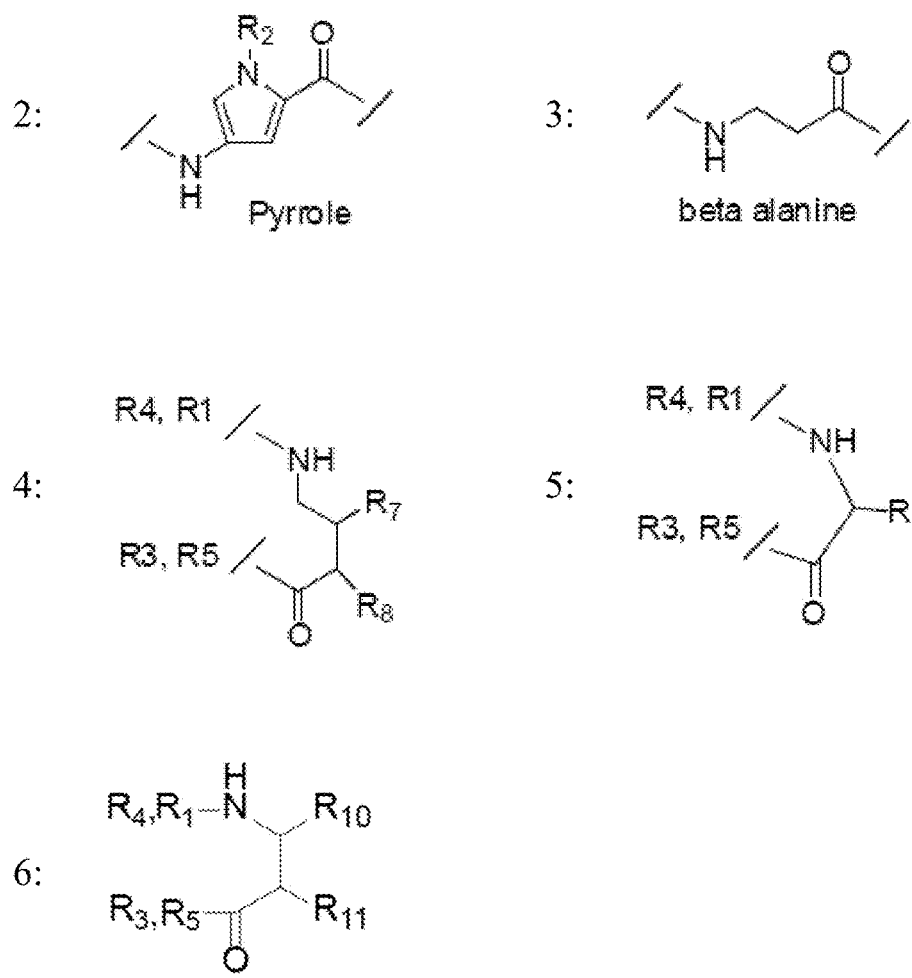

FIG. 2: Structural elements of a polyamide shown in FIG. 1 are exemplified. A pyrrole of structure 2 may be replaced by a beta-alanine of structure 3 in certain embodiments.

Structures 4-6 are turnunits that may link each $R_3$ and $R_4$, and/or each $R_1$ and $R_5$ in structure 1 to form a hairpin- or a cyclic-shaped molecule.

FIG. 3: Structural elements of a polyamide according to certain embodiments of the invention are exemplified. Each $R_7$, $R_8$, $R_9$, $R_{10}$, and $R_{11}$ in structures 4-6 may be independently selected from structures 7-17 according to certain embodiments.

FIG. 4: Structural elements of a polyamide according to certain embodiments of the invention are exemplified. Each $R_{13}$ (for example, in structures 10, 13, 15, and 17) may be independently selected from structures 18-29 according to certain embodiments.

Figure 5A:
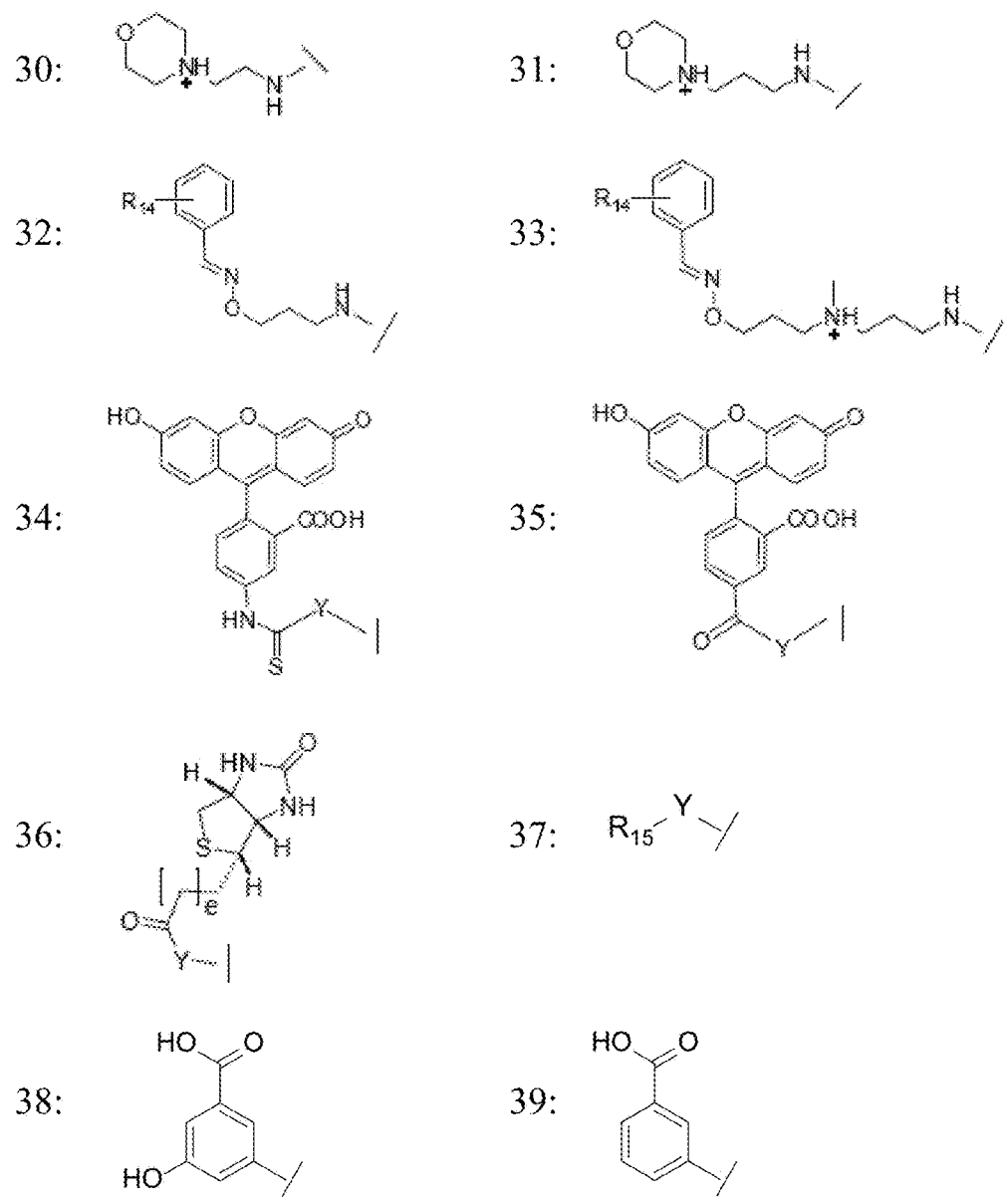

FIG. 5A-5B: Structural elements of a polyamide shown in FIG. 1 are exemplified. (A) Each $R_1$ and $R_4$ (for example, in structure 1) may be independently selected from structures 30-39 according to certain embodiments. (B) Each $R_1$ and $R_4$ (for example, in structure 1) may be independently selected from structures 30-37 according to certain embodiments. Each Y (for example, in structures 34-37) may be independently selected from structures 47-51 according to certain embodiments. Each $R_{15}$ (for example, in structure 37) is independently selected from structures 18-29 and 38-46. Each amide linkage of structure 52 that occurs in structures 35-37 may be independently replaced by a thiourea linkage of structure 53 or the reverse orientation of structure 52.

FIG. 6A-6D: (A) Structures 54 and 55 show polyamides according to certain embodiments of the invention. (B) Structures 56 and 57 show polyamides according to certain embodiments of the invention. (C) Structures 58 and 59 show polyamides according to certain embodiments of the invention. (D) Structure 60 shows a polyamide according to certain embodiments of the invention.

FIG. 7A-7F: (A) A polyamide according to certain embodiments of the invention is shown as structure 61 or ARE-1. (B) Cytotoxicity of ARE-1, Bic, and Enz in LNCaP/AR cells over 72 hours. (C) Cytotoxicity of ARE-1 in LREX' cells is not attenuated by AR or GR activation by dihydrotestosterone (DHT) or dexamethasone (Dex), respectively. Samples treated with ARE-1 alone are labeled as NT. (D) Top: cytotoxicity of ARE-1 in VCaP cells is similarly unaffected by AR and/or GR activation. Bottom: long-term incubation of ARE-1 or enzalutamide (Enz) in VCaP cells. Error bars are SEM. *$p<0.05$. (E) 72 hr cytotoxicity of ARE-1 combined with abiraterone acetate (Abi), bicalutamide (Bic), docetaxel (Doc), and enzalutamide (Enz) in LNCaP/AR cells. Determined by CellTiter-Glo assay. (F) Data from E normalized to untreated or treatment with single agent. Error bars are SEM. *$p<0.05$; **$p<0.005$.

FIG. 8A-8B: (A) Chemical structure of ARE-1 and ARE-1-FITC. (B) Nuclear uptake of ARE-1-FITC in LNCaP/AR, LREX', and VCaP cells.

FIG. 9A-9D: (A) Effects of ARE-1, Bic, and Enz on DHT induced KLK3 mRNA in LNCaP/AR cells (top), and baseline (charcoal stripped media) (bottom). (B) Effects of ARE-1 and Enz against select genes co-regulated by AR and GR in LREX' cells. (C) GSEA analysis in LREX' cells. Top: DHT enriches for the Androgen Response. Bottom: ARE-1 with DHT negatively enriches for Androgen Response and the UV Response Down. (D) ARE-1 treatment of LNCaP cells negatively enriches for Androgen Response and the UV Response Down. *$p<0.05$.

Figure 10:
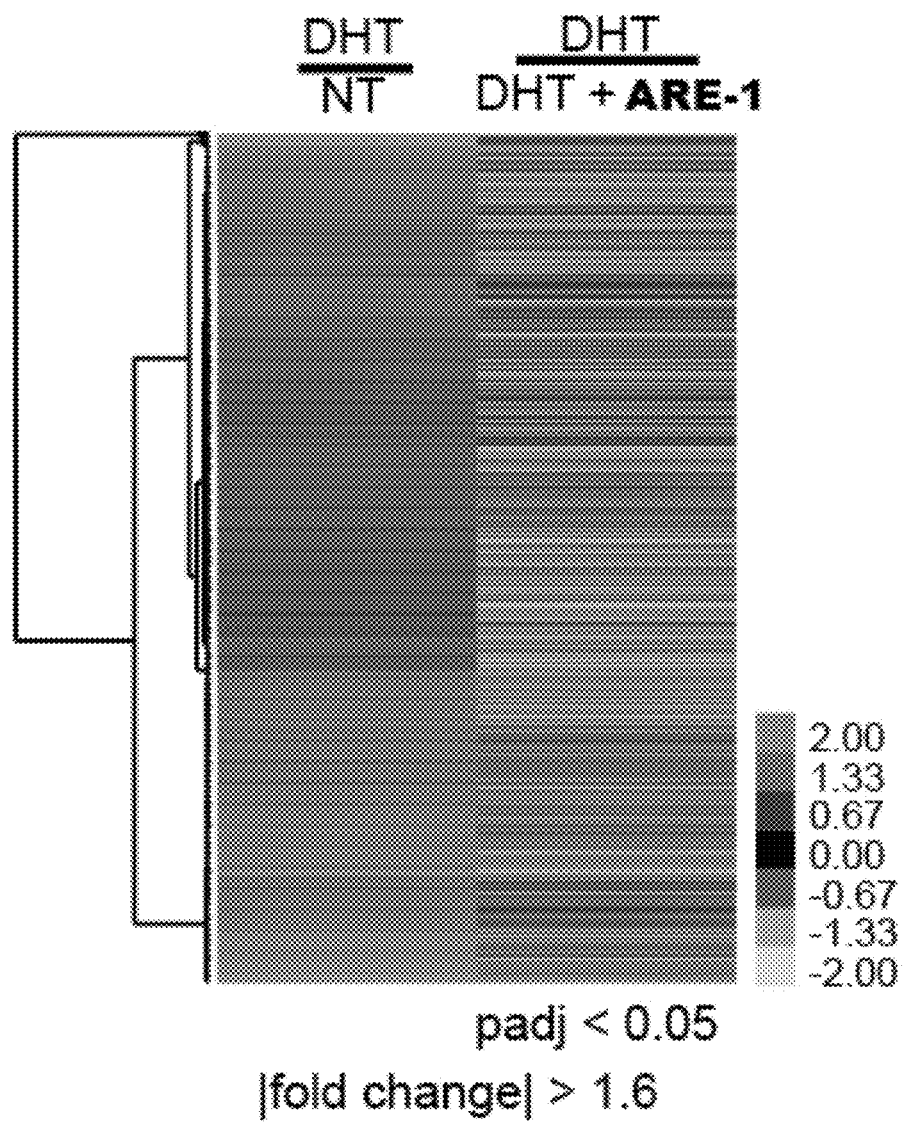

FIG. 10: Heatmap of gene expression profile of LREX' cells for conditions DHT/NT and DHT/DHT+ARE-1.

Figure 11A:
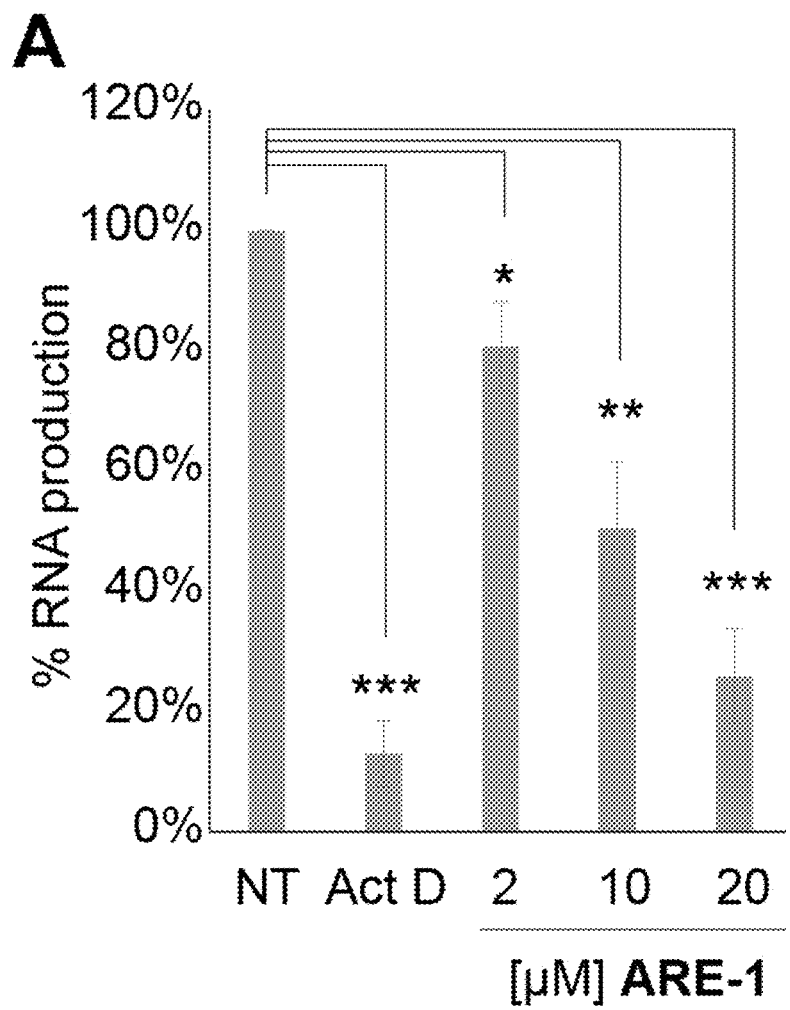
Figure 11B:
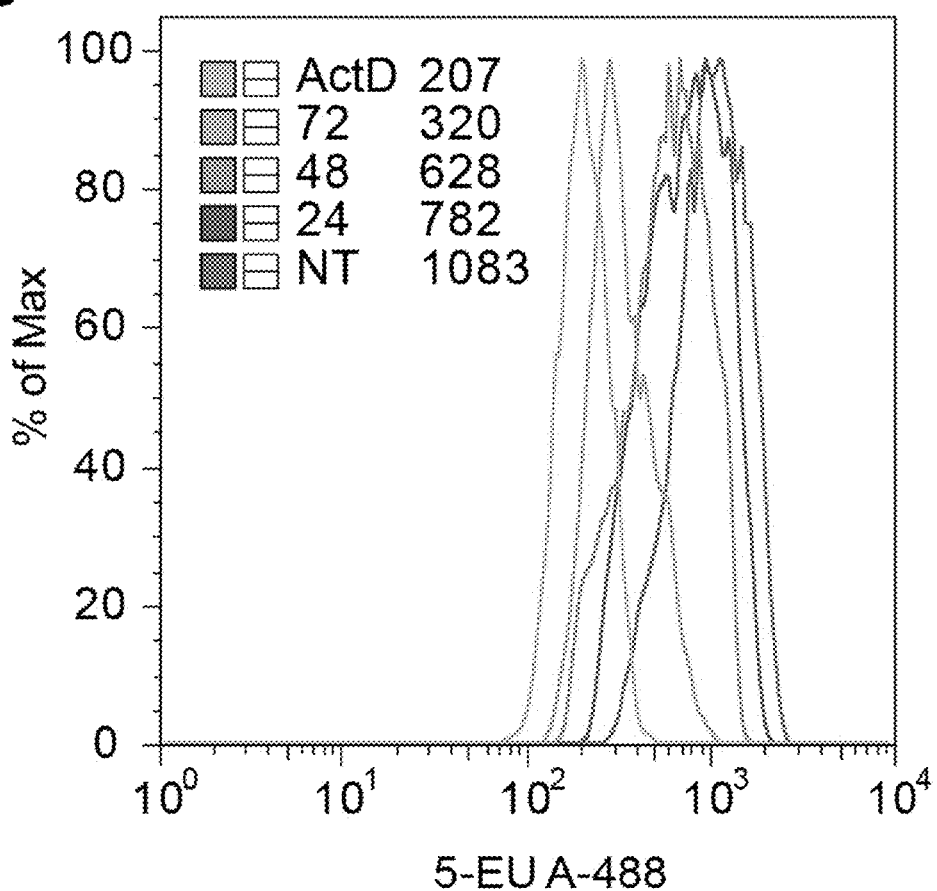
Figure 11C:
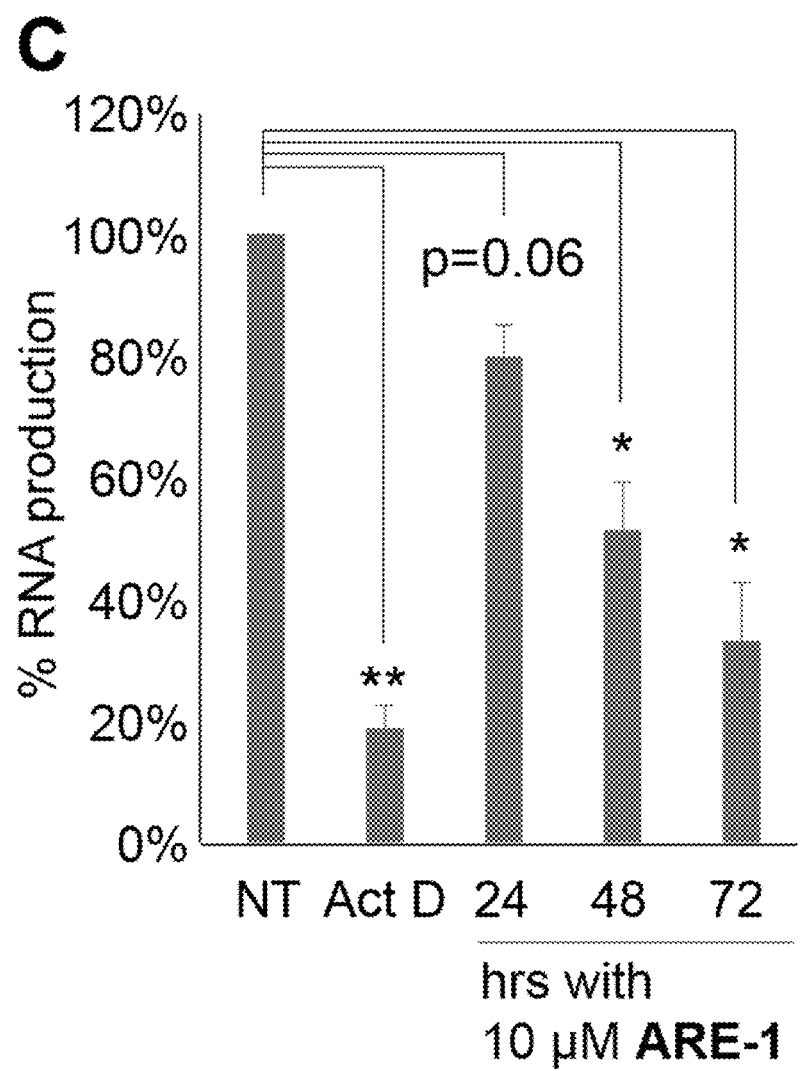

FIG. 11A-11C: (A) Nascent RNA in LREX' cells treated with ARE-1 for 48 hours. Actinomycin D (Act D):positive control. (B) Nascent RNA in LREX' cells by flow cytometry after treatment with 10 µM ARE-1 for 24, 48, 72 hours. (C) Composite of flow cytometry results. Error bars are SEM. *$p<0.05$; $p<0.005$; *$p<0.0005$.

Figure 12A:
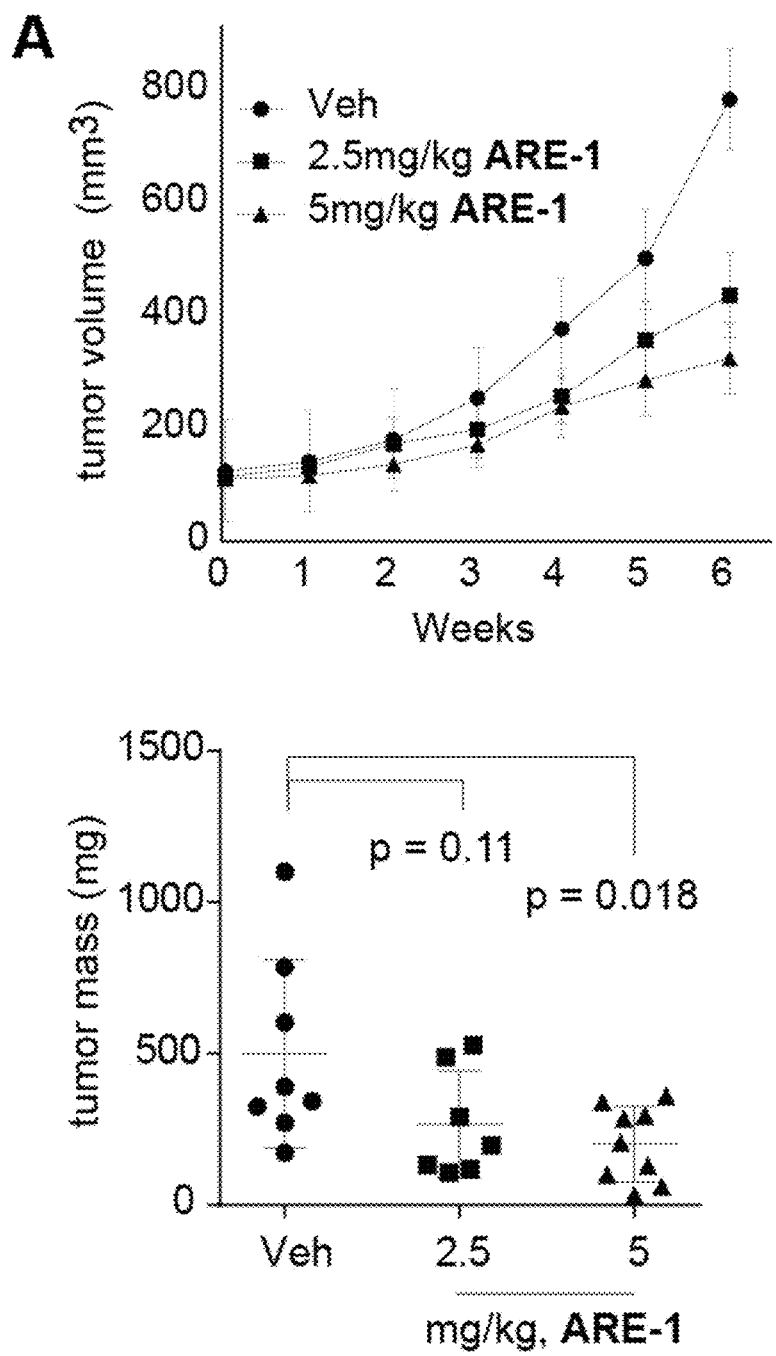
Figure 12B:
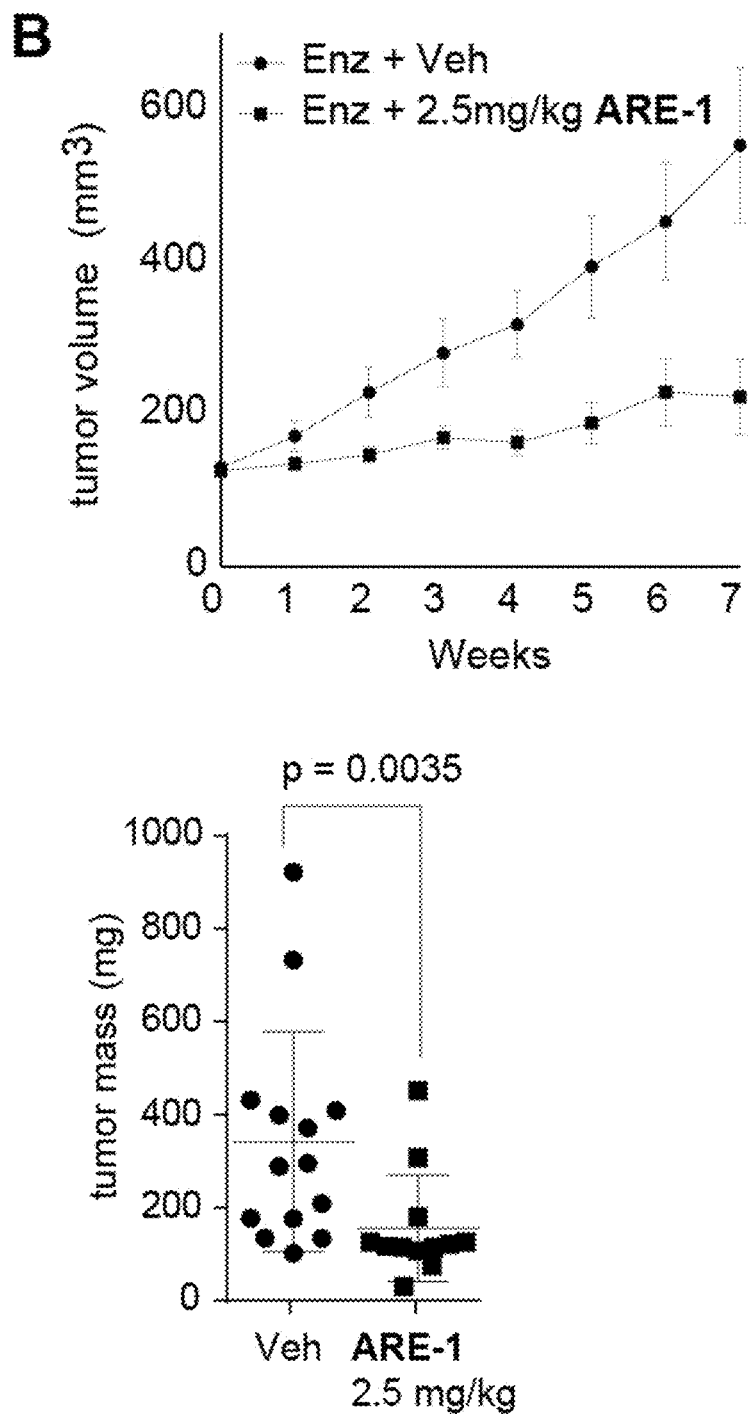
Figure 12C:
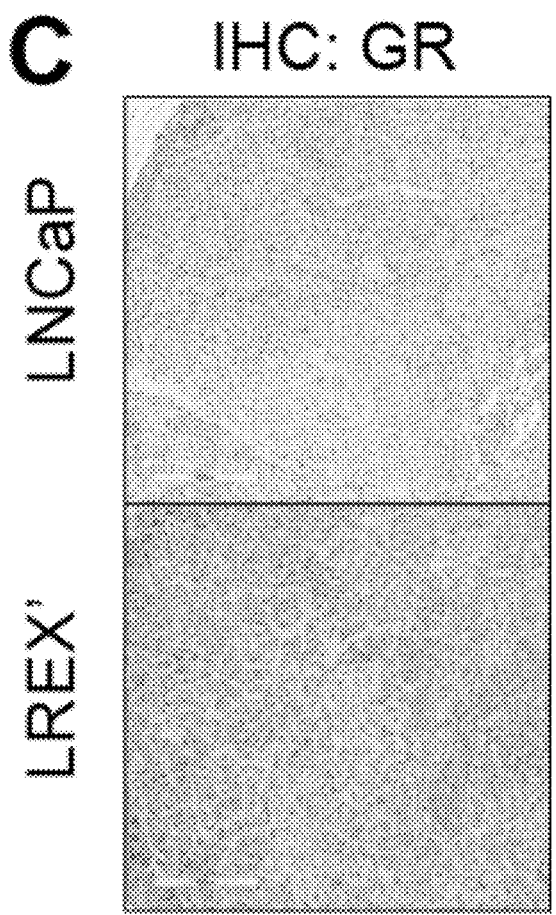

FIG. 12A-12C: Mice were treated three times per week with ARE-1 subcutaneously to flanks opposite engrafted tumor. (A) (Top) tumor volumes and (bottom) final tumor masses of VCaP xenografts treated with vehicle (Veh) (n=8), 2.5 mg/kg (n=7), and 5 mg/kg (n=8) ARE-1. (B) (Top) tumor volumes and (bottom) final tumor masses of LREX' xenografts in castrated animals treated daily with 10 mg/kg Enz and Veh (n=14) or Enz and 2.5 mg/kg ARE-1 (n=12). (C) GR staining of LREX' and LNCaP tumors. All LREX' tumors stained for GR. Error bars for tumor volumes are SEM. Whisker plots represent means, standard deviations.

FIG. 13A-13D: (A) Weights of VCaP tumor bearing animals treated with ARE-1. (B) Weights of LREX' tumor bearing animals treated with Enz or Enz+ARE-1. (C) Expression of KLK3 mRNA in tumor tissue. (D) TUNEL and Ki67 analysis of LREX' tumors. For animal weights and KLK3 expression, error bars are standard errors of the mean. Whisker plots for TUNEL and Ki67 staining represent means, quartiles, and maxima/minima. *$p<0.05$; $p<0.005$; *$p<0.0005$.

Figure 14:
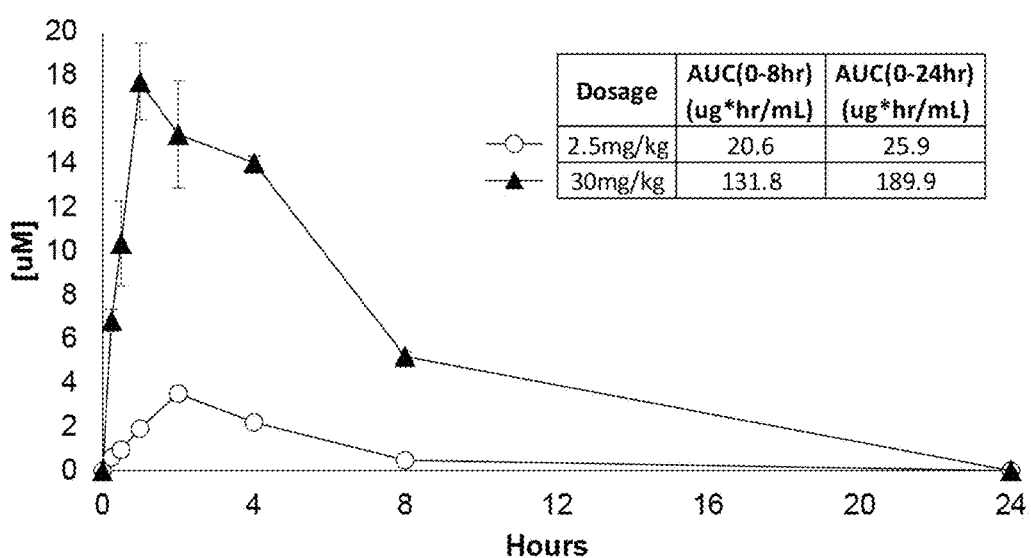

FIG. 14: Plasma concentration of ARE-1 at 2.5 mg/kg and 30 mg/kg in LREX' tumor bearing SCID mice and C57BL6/J mice, respectively.

5.0 DETAILED DESCRIPTION OF THE INVENTION

The present invention relates to combination drugs for the treatment of prostate cancer and related methods. In certain embodiments, a combination drug of the current invention comprises a polyamide and a prostate agent. In certain embodiments, a combination drug of the current invention comprises a polyamide, a prostate agent, and a pharmaceutically acceptable carrier. In certain embodiments, a combination drug of the current invention comprises one, two, three, four, five, six, seven, eight, nine, or ten, or 1-10, or 1-5, or 2-5 different polyamides and one, two, three, four, five, six, seven, eight, nine, or ten, or 1-10, or 1-5, or 2-5 different prostate agents. Two polyamides, and two prostate agents, are different if they have a different chemical structure.

In certain embodiments, a combination drug of the current invention essentially consists of a polyamide and a prostate agent. In certain embodiments, a combination drug of the current invention essentially consists of a polyamide, a prostate agent, and a pharmaceutically acceptable carrier. In certain embodiments, a combination drug of the current invention essentially consists of one, two, three, four, five, six, seven, eight, nine, or ten, or 1-10, or 1-5, or 2-5 different polyamides and one, two, three, four, five, six, seven, eight, nine, or ten, or 1-10, or 1-5, or 2-5 different prostate agents.

In certain embodiments, a combination drug of the current invention may be prepared as one preparation, containing all polyamide components and all prostate agent components. In certain embodiments, a combination drug of the current invention may be prepared as more than one preparation, for example, as two preparations, preferably with one preparation containing all polyamide components and a second preparation containing all prostate agent components, or as more than two preparations, for example, three, four, five, six or more preparations.

In certain embodiments, a combination drug of the current invention can be administered to a patient, including a human and/or an animal, for the treatment of prostate cancer, for example, through a parenteral route and/or orally. In certain embodiments, a combination drug of the current invention can be administered to a patient by administering all preparations of the combination drug at the same time or as much at the same time as is possible, or all preparations are administered over time, for example, over 1 hour, 2 hours, 3 hours, 6 hours, 12 hours, 1 day, 2 days, or longer or within a range of time defined by any two of the aforementioned time points. In certain embodiments, preparations containing single drugs or different combinations of drugs may be administered on different schedules.

5.1 Polyamides of a Combination Drug of the Invention

A polyamide of a combination drug of the current invention, in certain embodiments, is capable of modulating AR- and GR-mediated gene regulation in a cell. Polyamides of the current invention, in certain embodiments, are capable of entering a cell and of binding ARE and/or GRE in the genome of the cell so as to inhibit binding of NHRs to the ARE and/or GRE. Polyamides of the current invention, in certain embodiments, are capable of binding the sequence 5'-WGWWCW-3' (W=A or T), which is found in a subset of ARE and GRE half-sites. Polyamides of the current invention, in certain embodiments, are capable of binding the sequence 5'-WGGWCW-3' (W=A or T), which is found in a subset of ARE and GRE half-sites.

Polyamides of a combination drug of the current invention, in certain embodiments, comprise a structure 1, wherein each X in structure 1 may be independently selected from a CH, N, CF, COH, or COMe (each p independently selected from 0 and 1), wherein each $R_2$ is independently selected from H, a $C_{1-10}$ alkyl, a $C_{1-10}$ alkenyl, a $C_{1-10}$ alkynyl, —(CH2)$_q$—NH—$R_6$ (each q independently selected from 1-10). Each $R_6$ is independently selected from structures 18-29. Any $R_2$ may be covalently linked to another $R_2$ by a $C_{1-10}$ alkyl, a $C_{1-10}$ alkenyl, or a $C_{1-10}$ alkynyl linker to form an H- or U-shaped molecule. In structure 1, each pyrrole unit of structure 2 may be independently replaced by a beta-alanine of structure 3. Each $R_3$ and $R_4$, and/or each $R_1$ and $R_5$ in structure 1 may be covalently linked by a turn of any one of structures 4-6 to form a hairpin- or a cyclic-shaped molecule. Each $R_1$ and $R_4$ (for example, in structure 1) may also be independently selected from structures 30-37. Each $R_7$, $R_8$, $R_9$, $R_{10}$, and $R_{11}$ in structures 4-6 may be independently selected from an R or S isomer, and is independently selected from OH, OMe, OEt, F, Cl, Br, I, and structures 7-17 (each s independently selected from 1-10). Each $R_{12}$ (for example, in structures 14 and 16) is independently selected from H, OH, OMe, OEt, NH2, NHMe, CH3, and structures 30-37. Each $R_{13}$ (for example, in structures 10, 13, 15, and 17) is independently selected from structures 18-29. Each Y is independently selected from structures 47-51. Each e, g, and t is independently selected from 1-10. Each $R_{14}$ represents one, two, three, four, or five sidechains of the ring (up to the maximum number) with each $R_{14}$ being independently selected from H, OH, OMe, OEt, CH$_3$, CH$_2$CH$_3$ NH$_2$, F, Cl, Br, I, COOH, COOMe, COOEt, CONH$_2$, CN, NCOMe, NO$_2$, SO$_3$, PO$_4$, and CH$_2$PO$_3$, and each amide linkage of structure 52 that occurs in structures 35-37 may be independently replaced by a thiourea linkage of structure 53 or the reverse orientation of structure 52. Each $R_{15}$ (for example, in structure 37) is independently selected from structures 18-29 and 38-46. Polyamides of the current invention, in certain preferred embodiments, comprise any one or more of structures 54-61.

Polyamides of the present invention may be synthesized by any method known in the art, for example, by solid phase or solution phase methods using 4-(Boc-amino)-1-methyl-pyrrole-2-carboxylic acid, 4-(Boc-amino)-1-methyl-1H-imidazole-2-carboxylic acid, and derivatives thereof. For solid phase synthesis, polyamides are cleaved from the support, and purified by reverse-phase HPLC, as well known in the art. The identity and purity of the polyamides may be verified using any of a variety of analytical techniques available to one skilled in the art such as $^1$H-NMR, analytical HPLC, and/or matrix-assisted laser-desorption ionization time-of-flight mass spectrometry (MALDI-TOF MS-monoisotropic). A polyamide of the invention, in certain embodiments, may also comprise a protective group useful for purposes of polyamide synthesis, in certain other embodiments, a tail-polyamide does not comprise a protective group. Useful protective groups are known to those of skill in the art.

The aliphatic functionalities of linkable units can be provided, for example, by condensation of structures 47-51 during synthesis of the polyamide by methods well known in the art. Linkable units are typically supplied as amino acids, desamino acids, or descarboxy amino acids prior to amide bond formation by condensation methods well known in the art to form linking amide groups. The term "amino acid" refers to an organic molecule containing both an amino group (NH$_2$) and a carboxylic acid (COOH). The term "desamino" refers to an amino acid from which the amino functionality has been removed. The term "descarboxy" refers to an amino acid from which the carboxylic acid functionality has been removed. The term "chemical probe" refers to chemical functionalities having properties that facilitate location and identification of polyamides functionalized (including, for example, covalently bonded) by such chemical probes. A chemical probe does not include fluorescein in some embodiments. Methods of conjugating chemical probes to polyamides of the invention are well known in the art.

Polyamides may be synthesized by any method known in the art, including methods discussed herein. Methods of synthesizing organic compounds that are useful in synthesizing a tail-polyamide of the invention are discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are expressly incorporated herein by reference in their entireties.

5.2 Prostate Agents of a Combination Drug of the Invention

A prostate agent of a combination drug of the current invention, in certain embodiments, comprises a hormone therapeutic, an anti-androgen, a cytochrome P17 inhibitor, a taxane, and/or an inhibitor of AR nuclear translocation. In certain embodiments, a hormone therapeutic may comprise histrelin, triptorelin, goserelin, leuprolide (for example, Lupron, Eligard, and/or Leuprolide acetate), and/or degarelix. In certain embodiments, an anti-androgen may comprise flutamide, nilutamide, bicalutamide, enzalutamide, apalutamide, darolutamide, proxalutamide, and/or cyproterone acetate. In certain embodiments, a cytochrome P17 inhibitor may comprise ketoconazole, abiraterone acetate, orteronel, and/or seviteronel. In certain embodiments, a taxane may comprise cabazitaxel, docetaxel, and/or paclitaxel. In certain embodiments, an inhibitor of AR nuclear translocation may comprise enzalutamide, apalutamide, darolutamide, docetaxel, proxalutamide, cabazitaxel, and/or paclitaxel.

5.3 Quantitative Composition of a Combination Drug of the Invention

In certain embodiments, a combination drug of the current invention comprises a polyamide and a prostate agent in equal concentration. In certain embodiments, a combination drug of the current invention comprises a polyamide and a prostate agent in the same or about the same concentration or amount. In certain embodiments, a combination drug of the current invention comprises a polyamide at 1.5 times the concentration or amount of a prostate agent in the drug, or about 1.5 times, or 2-5 times or about 2-5 times, or 2-10 times or about 2-10 times, or 4-20 times or about 4-20 times, or 5-10 times or about 5-10 times, or an amount within a range defined by any two of the aforementioned ranges. In certain embodiments, a combination drug of the current invention comprises a prostate agent at 1.5 times the concentration or amount of a polyamide in the drug, or about 1.5 times, or 2-5 times or about 2-5 times, or 2-10 times or about 2-10 times, or 4-20 times or about 4-20 times, or 5-10 times or about 5-10 times, or an amount within a range defined by any two of the aforementioned ranges. Concentration can be measured, for example, in molarity, and amounts can be measured, for example, in mole. In certain embodiments, a combination drug of the current invention comprises a polyamide and a prostate agent, each comprising 5% to 95% of the total weight of the active ingredients in the administered dose (active ingredients being the polyamide(s) and prostate agent(s) in the combination drug), such that the sum of all polyamides and all prostate agents is 100% of the active ingredients in the administered dose.

5.4 Modulation of Gene Expression Using Polyamides of a Combination Drug of the Invention A polyamide of a combination drug of the invention is useful for modulating the expression of a gene. A polyamide of the invention in certain embodiments is capable of modulating the expression of a gene in a cell, preferably a living cell, and most preferably a cell in a higher organism, for example, a human, an animal, a dog, a cat, a pet, a farm animal, a cow, a pig, a chicken, a fish, or any other animal, or a plant. A polyamide of the invention in certain embodiments is capable of entering a cell and preferably the nucleus of the cell. In certain embodiments, a polyamide of the invention is useful for modulating gene expression in a cell in culture. In certain other embodiments, a polyamide of the invention is useful for modulating gene expression in a patient to ameliorate a disease symptom and/or to modulate a physiological process, for example, cell behavior, cell growth, cell secretion, cell signaling, and/or cell death, or any other process.

A polyamide of a combination drug of the present invention is capable of binding double stranded (for example, duplex) DNA at a specific sequence (for example, the target DNA sequence or target sequence or target site) with high affinity and selectivity. A recitation of a sequence of DNA herein contemplates the recited single-stranded DNA, the complementary (for example, Watson-Crick) sequence, and the duplex molecule comprising the recited and complementary strands of DNA.

A target site for a polyamide of the invention is determined by the order of pyrrole and imidazole amino acid composition based on established pyrrole-imidazole polyamide to DNA pairing rules in the minor groove. For example, the pairing of an imidazole amino acid across from a pyrrole amino acid will allow the nitrogen on the imidazole to hydrogen bond with the guanine N2-hydrogen such that the imidazole-pyrrole pairing recognizes a G-C base pair. The pairing of a pyrrole amino acid across from another pyrrole amino acid or across from a β-alanine amino acid will recognize T-A or A-T. The linker unit (L) as defined by structures 4-6, and derivatives thereof, will recognize T-A or A-T. And the C-terminal tail unit (C), defined by structures 30-37, and derivatives thereof, will recognize T-A or A-T. In certain embodiments, the target site of a polyamide of the amino acid composition Im-Py-Py-Py-L-Im-Py-Py-Py-C is 5'-WGWWCW-3'. In certain embodiments, the target site of a polyamide of the amino acid composition Im-Im-Py-Py-L-Im-Py-Py-Py-C is 5'-WGGWCW-3'. In certain embodiments, the target site for a pyrrole-imidazole polyamide may be found in an ARE and/or a GRE. An ARE, in certain embodiments, comprises a sequence of 5-WGWWCW-3' (W=A or T). In certain other embodiments, an ARE comprises six base pair half sites of the sequences 5'-TGTTCT-3', 5'-NGWACW-3' and 5'-TGTYCN-3' (with N=A, T, C, or G; and W=A or T; and Y=G or A), which may be a functional ARE without the presence of the full 15 base pair ARE present. Background on the ARE can be found in Roche P J et al., A consensus DNA-binding site for the androgen receptor. Mol Endocrinol. 1992 December; 6(12):2229-35; Massie C E et al., New androgen receptor genomic targets show an interaction with the ETS1 transcription factor. EMBO Rep. 2007 September; 8(9):871-8, which are incorporated herein by reference. A GRE, in certain embodiments, comprises the half-site of the sequence 5'-TGTTCT-3'. Proteins of the nuclear hormone receptor family of transcription factors have structures consisting of a ligand binding domain, an amino-terminal domain, a hinge domain, and a DNA binding domain. The DNA binding domain is largely conserved between the different nuclear hormone receptors, contains two modules of zinc coordinated by four cysteines, and is related to the classical Cys-2-His-2 zinc finger motifs of DNA binding proteins.

Most nuclear hormone receptors bind as homo- or heterodimmers to their respective response elements on DNA at particular gene regulatory sequences for their target genes. The steroid receptor subgroup, including androgen receptor, estrogen receptor, glucocorticoid receptor, progesterone receptor, and mineralocorticoid receptor, each bind typically as homo-dimers. The response elements typically consist of two six base pair sequences, "half-sites," that are separated by an intervening spacer sequence of one to five, usually three, nucleotides. For most nuclear receptor response elements, the first and sixth base pairs are both either A-T or T-A pairs, moving from 5' to 3'. The second and fifth are G-C and C-G, respectively, moving from 5' to 3'. The nucleotides at the third and fourth positions vary depending on the particular receptor, and the particular response element. The ARE and GRE half sites are often of the sequence 5'-TGT-TCT-3', 5'-NGWACW-3', or 5'-TGT(G/T/A)CN-3', where W=A or T, and N=A, T, G, or C. The half sites for the response elements are often oriented as palindromes or semi-palindromes about the intervening spacer sequence. (Khorasanizadeh S, Rastinejad F. Nuclear-receptor interactions on DNA-response elements. Trends Biochem Sci. 2001 June; 26(6):384-90, incorporated herein by reference.)

DNA binding polyamides composed of eight heterocyclic rings of imidazole or pyrrole linked by amide linkages can be designed to bind to the six base pair half sites of nuclear receptors. A polyamide could be designed to bind at one or both half sites for a particular response element, or two different polyamides could be designed to bind at each half site for a particular response element, or two or more polyamides could be designed to bind at one or more of the response elements for a nuclear receptor at different loci in the genome.

A DNA binding polyamide that is targeted to bind to an ARE or GRE, or another binding site for some other nuclear receptor, includes in its structure an imidazole opposite a pyrrole in the minor groove at the second base pair (a G-C pair) of the six base pair half site such that the exocyclic amine of the guanine can hydrogen bond with the lone pair nitrogen of the imidazole at this position. Additionally, such a polyamide would also include in its structure a pyrrole opposite an imidazole at the fifth base pair (a C-G pair), likewise so that the exocyclic amine of the guanine can hydrogen bond with the lone pair nitrogen of the imidazole at this position. The imidazole or pyrrole content at positions three and four of the six-base pair half site are determined by the particular base pair sequence that is to be targeted such that a G-C pair is presented with an imidazole-pyrrole pair, a C-G pair is presented with a pyrrole-imidazole pair, and either an A-T or T-A is presented with a pyrrole-pyrrole pair. For example, a polyamide targeted to an ARE containing a half site of the sequence 5'-TGTGCA-3' would in part comprise a pyrrole opposite a pyrrole at the third position T-A base pair, and an imidazole opposite a pyrrole at the G-C base pair at the fourth position. In another example, a polyamide targeted to a GRE containing the half site of the sequence 5'-TGTTCT-3' would in part comprise a pyrrole opposite a pyrrole at both the T-A base pairs at the third and fourth positions. For polyamides targeted to bind at such half sites, the tail and turn of the polyamide lie over the first and sixth positions of the half site.

As used herein, "subnanomolar affinity" means binding that is characterized by a dissociation constant, $K_d$, of less than 1 nM, as measured by DNase I footprint titration. In certain preferred embodiments, a polyamide of the present invention is characterized by subnanomolar affinity for ARE and/or GRE and/or the target DNA sequence 5'-WGW-WCW-3'. As used herein, the "selectivity" of the binding of a polyamide to a target sequence (for example, an ARE and/or an GRE) is the ratio of the dissociation constant, $K_d$, as measured by DNase I footprint titration, when binding the polyamide to a mismatch DNA sequence divided by the corresponding dissociation constant when binding the polyamide to the target sequence. In certain preferred embodiments, polyamides of the present invention are characterized by a selectivity of 3 or greater, or about 3 or greater, or 10 or greater, or about 10 or greater, or 20 or greater, or about 20 or greater, or 50 or greater, or about 50 or greater, or 100 or greater, or about 100 or greater, or an amount within a range defined by any two of the aforementioned values.

In certain preferred embodiments, a polyamide of the invention has at least 5-fold greater affinity for a target sequence (for example, an ARE and/or an GRE) than for a site differing from the target site by one, two, or three nucleotides, or at least 10-fold, or at least 20-fold, or at least 50-fold, or at least 100-fold, or at least 200-fold, or at least 500-fold or within a range defined by any two of the aforementioned values. Preferably, a polyamide of the invention will interact with an ARE and/or GRE with an affinity, as measured by DNase I footprint titration, of less than 100 nM, or preferably less than 50 nM, or preferably less than 25 nM, or preferably less than 15 nM, or preferably less than 10 nM, or preferably less than 5 nM, or preferably less than 1 nM, or preferably less than 0.2 nM, or preferably less than 0.1 nM (but not zero) or within a range defined by any two of the aforementioned values.

In certain embodiments, a polyamide of the invention has a binding affinity $K_a$ for an ARE and/or GRE that is greater than $10^8$ M$^{-1}$, or preferably greater than $2\times10$ M$^{-1}$, or preferably greater than $5\times10^8$ M$^{-1}$, or preferably greater than $10^9$ M$^{-1}$, or preferably greater than $2\times10^9$ M$^{-1}$, or preferably greater than $5\times10^9$ M$^{-1}$, or preferably greater than $10^{10}$ M$^{-1}$, or preferably greater than $2\times10^{10}$ M$^{-1}$, or preferably greater than $5\times10^{10}$ M$^{-1}$, or preferably greater than $10^{11}$ M$^{-1}$ or within a range defined by any two of the aforementioned values. The reduction in affinity of a polyamide of the invention to an ARE and/or GRE with a mismatch of one, two or three nucleotides, when compared to ARE and/or GRE without a mismatch, in certain embodiments, is at least 3 fold, at least 5 fold, at least 10 fold, at least 20 fold, at least 50 fold, or at least 100 fold, or more, or an amount within a range defined by any two of the aforementioned values. The affinity of a polynucleotide of the invention to DNA (or another molecule) can be determined by any method known in the art and as discussed herein.

A polyamide of the invention, in certain embodiments, can be examined to determine its affinity for its target DNA sequence and at mismatched and random sites, if desired. The affinity can be determined using DNase I footprint analysis, as discussed herein. A polyamide of the invention, in certain embodiments, can also be examined to determine its ability to modulate gene expression, for example, by using an ARE and/or GRE involved in regulating the expression of a gene. For example, a polyamide may be administered to cells in culture at varying concentrations (e.g., at 0.1 μM, 0.3 μM, 1 μM, 3 μM, 10 μM, 30 μM, 100 μM, 300 μM, or 1 mM, or an amount within a range defined by any two of the aforementioned values) and the expression of a gene that depends on an ARE and/or GRE may be determined by measuring levels of mRNA (messenger RNA) compared to mRNA levels in the absence of the polyamide. The analysis may be carried out, for example, as discussed in the examples below. An analysis of a polyamide's ability to modulate gene expression may be carried out in different cell types, for example, as described in Edelson et al., 2004, Nucleic Acids Res. 32:2802-2818, expressly incorporated herein by reference. Other methods to analyze a polyamide's ability to modulate gene expression include the use of luciferase, protein quantitation, observing morphological and/or phenotypic changes, which are known to those of skill in the art.

Methods for the analysis of polyamides' ability to bind DNA and to modulate gene expression are further discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are expressly incorporated herein by reference in their entirety.

5.5 Polyamides of the Current Invention as Research Tools

A polyamide of the invention, in certain embodiments, may be used as a research tool. For example, a polyamide of the invention may be used to modulate the expression of genes involved in a disease in cell culture or in an animal, for example, by down-regulating a gene so that the cells or the animal exhibits one or more traits of the disease. Following such modulation, a drug candidate may be tested in the cell culture and/or the animal to determine if the drug candidate is capable of compensating for the effects of gene modulation.

In certain other embodiments, a polyamide may be used to test the effectiveness of analytical techniques in a cell and/or an animal, for example by modulating gene expression and by testing the technique's ability to detect the effects thereof.

5.6 Therapeutic Applications of Combination Drugs of the Current Invention

A combination drug of the current invention, in certain embodiments, may be used in the treatment, including the prevention, of prostate cancer in humans and/or animals. It is contemplated that these compounds may be used independently or in conjunction with inactive excipients or active ingredients. As used herein, the term "agent" refers to compounds of the invention or compositions thereof comprising active and/or inactive ingredients.

In certain embodiments, a combination drug of the current invention may be used to modulate the expression of a gene, the expression of which depends at least in part on an ARE and/or GRE. In certain embodiments, polyamides of the invention may be used to modulate a gene with one, two, three, four, five, six or more AREs and/or GREs in a regulatory sequence of the gene, for example, in a promoter of the gene or an enhancer of the gene. A regulatory sequence of a gene may be within the gene (for example, in an intron, or in a 5 prime or 3 prime untranslated region), 5 prime (upstream) of the gene (for example, as part of a promoter that is located upstream of, and adjacent to or close to, the transcription initiation site), or 3 prime (downstream) of the gene (for example, 3 prime of the transcription termination site).

In certain embodiments, polyamides of the invention may be used to modulate the expression the PSA (KLK3) gene (prostate specific antigen), the KLK2 gene, the TMPRSS2 gene, the DHCR24 gene, the LOC89944 gene, the NNMT gene, the GSTM1 gene, the UNC13 gene, the BICD1 gene, the ENTPD5 gene, the PFKFB3 gene, the ARL7 gene, the FLJ2378 gene, the ATP2C1 gene, the C20orf167 gene, the SLC37A1 gene, the DOK4 gene, the FLJ14249 gene, the FLJ38482 gene, the TMEPAI gene, the ASAH1 gene, and/or the UNC5H2 gene. In certain embodiments, a polyamide of the present invention may be used to modulate gene expression, for example, by interfering with RNA polymerase II activity.

In certain embodiments, polyamides of the invention may be used to modulate the expression of a gene with an ARE, for example, a gene listed in Massie C E et al., New androgen receptor genomic targets show an interaction with the ETS1 transcription factor. EMBO Rep. 2007 September; 8(9):871-8; Bolton E C et al., Cell- and gene-specific regulation of primary target genes by the androgen receptor. Genes Dev. 2007 Aug. 15; 21(16):2005-17, which are expressly incorporated herein by reference for any purpose.

In certain embodiments, polyamides of the invention may be used to modulate the expression of a gene that is expressed in a tissue or organ, but that is not expressed in other tissues or organs, or that is expressed in other tissues at significantly lesser levels (for example, less than 20 percent, or less than 10 percent, or less than 5 percent), in other words a tissue-specific gene. A tissue-specific gene may be expressed in the prostate (prostate-specific gene).

In certain embodiments, combination drugs of the invention may be used to treat a disease. "Treating" as used herein refers to alleviation of at least one symptom associated with a disease (for example, cancer), or halt of further progression or worsening of such disease, or cause the regression of the disease, or prevention or prophylaxis of such disease. In certain embodiments, combination drugs of the invention may be used to treat cancer, prostate cancer, a prostate-specific disease, and/or a disease involving the expression of a gene that is regulated by an ARE and/or GRE (for example, prostate cancer, breast cancer, and/or ovarian cancer).

A combination drug of the invention, in certain embodiments, may be delivered to a patient in any way known in the art. The particular delivery mode selected will depend upon the combination drug selected, the condition being addressed, the severity of the condition, whether the procedure is therapeutic or prophylactic, and the dosage required for efficacy. Therapeutic delivery of a combination drug of the invention may be practiced using any mode of administration that is medically acceptable, meaning any mode that produces effective levels of the active compounds without causing clinically unacceptable adverse effects. Any dosage forms containing effective amounts are well within the bounds of routine experimentation and therefore, well within the scope of the instant invention. A therapeutically effective dose may vary depending upon the route of administration and dosage form. The administration may be, for example, oral, intraperitoneal, intra-cavity such as rectal or vaginal, transdermal, topical, nasal, inhalation, mucosal, interdermal, and/or parenteral routes. The term "parenteral" includes subcutaneous, intravenous, intramuscular, or infusion. In certain embodiments, it may be appropriate to administer the agent in a continuous infusion or as a subcutaneous injection every day, every two or several days, or once a week, or every several weeks, or once a month, or once every several months, or at a time interval within a range defined by any two of the aforementioned intervals. Intravenous or intramuscular routes may be preferred in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

Direct administration of a combination drug of the present invention to a designated site may be preferred for some methods provided herein. For example, treatment with a combination drug via topical administration in and around affected areas may be performed. In still other embodiments, a combination drug may be delivered by injection directly into the tissue with, for example, a biopsy needle and syringe for localized intratumoral administration.

Systemic administration may be preferred in some instances such as, for example, if the subject is known to have or is suspected of having metastases. In this embodiment, all tumor sites, whether primary or secondary, may receive the combination drug. Systemic delivery may be accomplished through for example, oral or parenteral administration. Inhalation may be used in either systemic or local delivery, as described below.

A polyamide and a prostate agent of a combination drug of the current invention, in certain embodiments, may be administered by the same mode of administration and/or in the same administration, and they may be administered in different modes of administration and/or in different administrations. For different modes of administration, one component of a combination drug may be administered orally, another component may be administered by IV infusion, another component may be administered by subcutaneous injection, or another mode of administration known in the art, and three or more components of a combination drug may be administered in three or more modes of administration.

A combination drug of the invention, in certain embodiments, is administered in therapeutically effective amounts. A therapeutically effective amount is an amount sufficient to delay the onset of, inhibit the progression of, or lead to the regression of the particular condition being treated, for example, prostate cancer. The effective amount will vary with the particular condition being addressed, the age and physical condition of the subject receiving therapy, the severity of the condition, the duration of the therapy, the nature of the concurrent or combination therapy (if any), the specific route of administration and like factors within the knowledge and expertise of the health practitioner. A therapeutically effective dose results in amelioration of at least one undesirable symptom. It is preferred generally that a maximum dose be used, that is, the highest safe dose according to sound medical judgment. Dosing amounts, dosing schedules, routes of administration and the like can be selected so as to affect bio-activity of the present compounds. Such determinations are routine and well known to one of ordinary skill in the art.

A therapeutically effective amount of a combination drug of the current invention typically varies from 0.01 mg/kg (weight of combination drug over weight of patient) to 2000 mg/kg, such as 0.01, 0.05, 0.1, 0.2, 0.5, 1, 2, 5, 10, 20, 50, 100, 200, 500, 1000, 1500, or 2000 mg/kg, or an amount within a range defined by any two of the aforementioned values, or preferably from 0.03 mg/kg to 200 mg/kg, and most preferably from 0.1 mg/kg to 50 mg/kg, in one or more dose administrations daily, for one or more days. In some embodiments, a combination drug is administered for more than 7 days, more than 10 days, more than 14 days, or more than 20 days. In still other embodiments, a combination drug is administered over a period of weeks, or months. In still other embodiments, a combination drug is delivered on alternate days. For example, the combination drug is delivered every two days, or every three days, or every four days, or every five days, or every six days, or on select days of the week, or every week, or every month.

In certain embodiments, a polyamide and a prostate drug component of a combination drug of the invention are administered in a dosage that is most suited for the polyamide and for the prostate drug.

A therapeutically effective amount of a polyamide of a combination drug of the current invention typically varies from 0.01 mg/kg (weight of polyamide over weight of patient) to 1000 mg/kg, such as 0.01, 0.05, 0.1, 0.2, 0.5, 1, 2, 5, 10, 20, 50, 100, 200, 500, or 1000 mg/kg, or an amount within a range defined by any two of the aforementioned values, or preferably from 0.1 mg/kg to 200 mg/kg, and most preferably from 0.2 mg/kg to 20 mg/kg, in one or more dose administrations daily, for one or more days. In some embodiments, a polyamide is administered for more than 7 days, more than 10 days, more than 14 days, or more than 20 days. In still other embodiments, a polyamide is administered over a period of weeks, or months. In still other embodiments, a polyamide is delivered on alternate days. For example, the polyamide is delivered every two days, or every three days, or every four days, or every five days, or every six days, or every week, or every month.

A therapeutically effective amount of a prostate drug of a combination drug of the current invention varies for different prostate drugs. The following are examples of suitable dosages for a prostate drug of a combination drug of the current invention.

For example, the prostate drug histrelin can be administered (for example subcutaneously) at a dosage of 5-500 mg over 12 months, or 10-400 mg over 12 months, or 15-300 mg over 12 months, or 20-200 mg over 12 months, or 25-100 mg over 12 months, or 30-70 mg over 12 months, or an amount within a range defined by any two of the aforementioned values, or preferably 50 mg over 12 months.

For example, the prostate drug triptorelin can be administered (for example intramuscularly) at a dosage of 2-250 mg over 6 months (or 1-125 mg over 3 months, or 0.3-45 mg over 1 month), or 4-150 mg over 6 months (or 2-80 mg over 3 months, or 0.6-30 mg over 1 month), or 6-100 mg over 6 months (or 3-60 mg over 3 months, or 0.8-25 mg over 1 month), or 8-60 mg over 6 months (or 4-40 mg over 3 months, or 1.0-17 mg over 1 month), or 10-45 mg over 6 months (or 5-25 mg over 3 months, or 1.4-12 mg over 1 month), or 15-35 mg over 6 months (or 8-17 mg over 3 months, or 2.5-8 mg over 1 month), or an amount within a range defined by any two of the aforementioned values, or preferably 22.5 mg over 6 months (or 11.25 mg over 3 months, or 3.75 mg over 1 month).

For example, the prostate drug goserelin can be administered (for example subcutaneously) at a dosage of 1-120 mg over 12 weeks (or 0.3-50 mg over 28 days), or 2.5-80 mg over 12 weeks (or 0.6-40 mg over 28 days), or 5-60 mg over 12 weeks (or 1.0-30 mg over 28 days), or 6-40 mg over 12 weeks (or 2.0-20 mg over 28 days), or 7-25 mg over 12 weeks (or 2.0-10 mg over 28 days), or 8-15 mg over 12 weeks (or 2.5-7 mg over 28 days), or an amount within a range defined by any two of the aforementioned values, or preferably 10.8 mg over 12 weeks (or 3.6 mg over 28 days).

For example, the prostate drug leuprolide can be administered at the following dosages for the three types of leuprolide known as Lupron, Eligard, and Leuprolide acetate. Lupron and Eligard can be administered (for example intramuscularly for Lupron and subcutaneously for Eligard) at a dosage of 0.75-75 mg over one month, or 1.5-50 mg over one month, or 3-30 mg over one month, or 4-20 mg over one month, or 5-15 mg over one month, or 6-12 mg over one month, or an amount within a range defined by any two of the aforementioned values, or preferably 7.5 mg over one month; and these dosages can be multiplied 3-times, 4-times, or six-times for administrations over 3, 4, or 6 months, respectively; and with each dosage given in 2, 3, or 4, but preferably in one administration over 1, 3, 4, or 6 months. Leuprolide acetate can be administered (for example subcutaneously) at a dosage of 0.1-10 mg per day, or 0.2-8 mg per day, or 0.3-6 mg per day, or 0.4-4 mg per day, or 0.5-3 mg per day, or 0.6-2 mg per day, or an amount within a range defined by any two of the aforementioned values, or preferably 1 mg per day.

For example, the prostate drug flutamide can be administered (for example orally) at a dosage of 15-2000 mg over 8 hours, or 30-1500 mg over 8 hours, or 50-1000 mg over 8 hours, or 80-500 mg over 8 hours, or 90-400 mg over 8 hours, or 100-350 mg over 8 hours, or an amount within a range defined by any two of the aforementioned values, or preferably 125-250 mg over 8 hours.

For example, the prostate drug nilutamide can be administered (for example orally) at a dosage of 30-3000 mg per day for 20-40 days and then half that dosage per day, or 60-2500 mg per day for 20-40 days and then half that dosage per day, or 100-2000 mg per day for 20-40 days and then half that dosage per day, or 140-1500 mg per day for 20-40 days and then half that dosage per day, or 180-1000 mg per day for 20-40 days and then half that dosage per day, or 225-750 mg per day for 20-40 days and then half that dosage per day, or 250-500 mg per day for 20-40 days and then half that dosage per day, or an amount within a range defined by any two of the aforementioned values, or preferably of 300 mg per day for 30 days and then half that dosage per day.

For example, the prostate drug bicalutamide can be administered (for example orally) at a dosage or 5-500 mg per day if the disease is local (and three times that dosage if the disease is advanced), or 10-400 mg per day if the disease is local (and three times that dosage if the disease is advanced), or 20-300 mg per day if the disease is local (and three times that dosage if the disease is advanced), or 30-200 mg per day if the disease is local (and three times that dosage if the disease is advanced), or 35-100 mg per day if the disease is local (and three times that dosage if the disease is advanced), or 35-75 mg per day if the disease is local (and three times that dosage if the disease is advanced), or an amount within a range defined by any two of the aforementioned values, or preferably 50 mg per day if the disease is local (and three times that dosage if the disease is advanced).

For example, the prostate drug enzalutamide can be administered (for example orally) at a dosage of 15-1600 mg per day, or 30-1200 mg per day, or 50-800 mg per day, or 80-500 mg per day, or 100-300 mg per day, or 120-250 mg per day, or an amount within a range defined by any two of the aforementioned values, or preferably 160 mg per day.

For example, the prostate drug apalutamide can be administered (for example orally) at a dosage of 25-2500 mg per day, or 50-2000 mg per day, or 75-1500 mg per day, or 100-1000 mg per day, or 120-500 mg per day, or 150-350 mg per day, or an amount within a range defined by any two of the aforementioned values, or preferably 240 mg per day.

For example, the prostate drug darolutamide can be administered at a dosage of 30-6000 mg in a single dose, or 60-4500 mg in a single dose, or 100-3000 mg in a single dose, or 150-2000 mg in a single dose, or 200-1200 mg in a single dose, or an amount within a range defined by any two of the aforementioned values, or preferably 300-600 mg in a single dose.

For example, the prostate drug proxalutamide can be administered at a dosage of 20-5000 mg in a single dose, or 40-3500 mg in a single dose, or 60-2000 mg in a single dose, or 100-1500 mg in a single dose, or 125-1000 mg in a single dose, or an amount within a range defined by any two of the aforementioned values, or preferably 200-500 mg in a single dose.

For example, the prostate drug cyproterone acetate can be administered (for example orally) at a dosage of 5-1500 mg per day, or 10-1000 mg per day, or 15-800 mg per day, or 25-600 mg per day, or 35-400 mg per day, or 40-250 mg per day, or an amount within a range defined by any two of the aforementioned values, or preferably 50-150 mg per day.

For example, the prostate drug ketoconazole can be administered (for example orally) at a dosage of 20-8000 mg per day, or 40-6000 mg per day, or 60-4000 mg per day, or 100-2000 mg per day, or 120-1500 mg per day, or 150-1200 mg per day, or an amount within a range defined by any two of the aforementioned values, or preferably 200-800 mg per day.

For example, the prostate drug abiraterone acetate can be administered (for example orally) at a dosage of 100-10000 mg per day, or 200-7500 mg per day, or 400-5000 mg per day, or 500-3000 mg per day, or 600-1500 mg per day, or an amount within a range defined by any two of the aforementioned values, or preferably 1000 mg per day.

For example, the prostate drug orteronel can be administered (for example orally) at a dosage of 30-4000 mg 2-times per day, or 60-3000 mg 2-times per day, or 90-2000 mg 2-times per day, or 125-1500 mg 2-times per day, or 150-1000 mg 2-times per day, or 200-700 mg 2-times per day, or an amount within a range defined by any two of the aforementioned values, or preferably 300-400 mg 2-times per day.

For example, the prostate drug seviteronel can be administered (for example orally) at a dosage of 40-4500 mg per day, or 80-3500 mg per day, or 125-2500 mg per day, or 175-1800 mg per day, or 225-1200 mg per day, or 275-800 mg per day, or an amount within a range defined by any two of the aforementioned values, or preferably 450 mg per day.

For example, the prostate drug cabazitaxel can be administered (for example intravenously by infusion once every three weeks, with each infusion applied over 1 hour) at a dosage of 2-250 mg per square meter of body surface area of the patient, or 4-200 mg per square meter of body surface area of the patient, or 8-150 mg per square meter of body surface area of the patient, or 12-100 mg per square meter of body surface area of the patient, or 15-75 mg per square meter of body surface area of the patient, or 18-50 mg per square meter of body surface area of the patient, or an amount within a range defined by any two of the aforementioned values, or preferably 25 mg per square meter of body surface area of the patient.

For example, the prostate drug docetaxel can be administered (for example intravenously by infusion once every three weeks, with each infusion applied over 1 hour) at a dosage of 7-750 mg per square meter of body surface area of the patient, or 15-600 mg per square meter of body surface area of the patient, or 25-450 mg per square meter of body surface area of the patient, or 35-300 mg per square meter of body surface area of the patient, or 45-200 mg per square meter of body surface area of the patient, or 60-150 mg per square meter of body surface area of the patient, or an amount within a range defined by any two of the aforementioned values, or preferably 75 mg per square meter of body surface area of the patient.

For example, the prostate drug paclitaxel can be administered (for example intravenously by infusion once every three weeks, with each infusion applied over 3 hours) at a dosage of 13-1350 mg per square meter of body surface area of the patient, or 30-1200 mg per square meter of body surface area of the patient, or 45-900 mg per square meter of body surface area of the patient, or 60-600 mg per square meter of body surface area of the patient, or 90-300 mg per square meter of body surface area of the patient, or an amount within a range defined by any two of the aforementioned values, or preferably 135 mg per square meter of body surface area of the patient.

A combination drug of the invention, in certain embodiments, is administered in prophylactically effective amounts. In these embodiments, a combination drug is administered in an amount effective to prevent and/or inhibit the development of an abnormal or undesirable condition or disease. For example, in connection with methods directed towards treating subjects having a condition characterized by abnormal mammalian cell proliferation, an effective amount to inhibit proliferation would be an amount sufficient to reduce or halt altogether the abnormal mammalian cell proliferation so as to slow, halt and/or regress the development of or the progression of a cell mass such as, for example, a tumor. As used in the embodiments, "inhibit" embraces all of the foregoing.

For example, in connection with methods directed to inhibition of mammalian cell proliferation, a therapeutically effective amount will be an amount necessary to extend the dormancy of micrometastases or to stabilize any residual primary tumor cells, or reduce the size of metastases following surgical or drug therapy.

Compositions presented herein may include a combination drug of the invention in combination with any standard physiologically and/or pharmaceutically acceptable carrier known in the art. The term "pharmaceutically acceptable carrier" as used herein means one or more compatible solid or liquid fillers, diluents or encapsulating substances which are suitable for administration to a subject. The term "carrier" denotes an organic or inorganic ingredient, natural or synthetic, which with the DNA-binding polymer is combined to facilitate delivery of the composition. The components of the pharmaceutical compositions also are capable of being co-mingled with the molecules of the present invention, and with each other, in a manner so as to not substantially impair the desired pharmaceutical efficacy. Pharmaceutically acceptable further means a non-toxic material that is compatible with a biological system such as a cell, cell culture, tissue, or organism. The particular carrier may vary depending on the route of therapeutic delivery.

Pharmaceutically acceptable carriers are well known in the art (see, for example, Remington, The Science and Practice of Pharmacy (21.sup.st Edition, Lippincott Williams and Wilkins, Philadelphia, Pa.) and The National Formulary (American Pharmaceutical Association, Washington, D.C.)). Pharmaceutically acceptable carriers include sugars (for example, lactose, sucrose, mannitol, and sorbitol), starches, cellulose preparations, calcium phosphates (for example, dicalcium phosphate, tricalcium phosphate and calcium hydrogen phosphate), sodium citrate, water, aqueous solutions (for example, saline, sodium chloride injection, Ringer's injection, dextrose injection, dextrose and sodium chloride injection, lactated Ringer's injection), alcohols (for example, ethyl alcohol, propyl alcohol, and benzyl alcohol), polyols (for example, glycerol, propylene glycol, and polyethylene glycol), organic esters (for example, ethyl oleate, phospholipids, and triglycerides), biodegradable polymers (for example, polylactide-polyglycolide, poly(orthoesters), and poly(anhydrides)), elastomeric matrices, liposomes, microspheres, oils (for example, corn, germ, olive, castor, sesame, cottonseed, soy bean, and groundnut), cocoa butter, waxes (for example, suppository waxes), paraffins, silicones, talc, and/or silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

Pharmaceutical compositions of the invention may, in certain embodiments, contain additional ingredients and/or materials commonly used in pharmaceutical compositions. These ingredients and materials are well known in the art and include any one or more of the following: fillers or extenders, such as starches, lactose, sucrose, glucose, mannitol, meglumine, and silicic acid; binders, such as carboxymethylcellulose, alginates, gelatin, polyvinyl pyrrolidone, hydroxypropylmethyl cellulose, sucrose and acacia; humectants, such as glycerol; disintegrating agents, such as agar-agar, calcium carbonate, potato or tapioca starch, alginic acid, certain silicates, sodium starch glycolate, cross-linked sodium carboxymethyl cellulose and sodium carbonate; solution retarding agents, such as paraffin; absorption accelerators, such as quaternary ammonium compounds including choline; wetting agents, such as cetyl alcohol and glycerol monostearate; absorbents, such as kaolin and bentonite clay; lubricants, such as talc, calcium stearate, magnesium stearate, solid polyethylene glycols, and sodium lauryl sulfate; suspending agents, such as ethoxylated isostearyl alcohols, polyoxyethylene sorbitol and sorbitan esters, microcrystalline cellulose, aluminum hydroxide, bentonite, agar-agar and tragacanth; buffering agents; excipients, such as lactose, milk sugars, polyethylene glycols, animal and vegetable fats, phospholipids, oils, waxes, paraffins, cocoa butter, starches, tragacanth, cellulose derivatives, polyethylene glycol, silicones, bentonites, silicic acid, talc, salicylate, zinc oxide, tromethamine, aluminum hydroxide, calcium silicates, and polyamide powder; inert diluents, such as water or other solvents; preservatives; surface-active agents such as polysorbates; dispersing agents; control-release or absorption-delaying agents, such as hydroxypropylmethyl cellulose, other polymer matrices, biodegradable polymers, liposomes, microspheres, aluminum monostearate, gelatin, and waxes; opacifying agents; adjuvants; wetting agents; emulsifying and suspending agents; solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, soy bean and sesame oils), glycerol, tetrahydrofuryl alcohol, polyethylene glycols and fatty acid esters of sorbitan; propellants, such as chlorofluorohydrocarbons and volatile unsubstituted hydrocarbons, such as butane and propane; antioxidants; agents which render the formulation isotonic with the blood of the intended recipient, such as sugars and sodium chloride; thickening agents; coating materials, such as lecithin; sweetening, flavoring, coloring, perfuming and/or preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutically acceptable carriers are discussed, for example, in U.S. Pat. Nos. 9,733,237; 9,730,947, and in references discussed in any one of these patents. All of these patents, and references discussed therein, are expressly incorporated herein by reference in their entirety.

Pharmaceutical compositions of the instant invention can be manufactured by methods well known in the art such as conventional granulating, mixing, dissolving, encapsulating, lyophilizing, emulsifying and/or levigating processes, among others. The compositions can be in the form of, for example, granules, powders, tablets, capsules, syrup, suppositories, injections, emulsions, elixirs, suspensions and/or solutions. The instant compositions can be formulated for various routes of administration, for example, by oral administration, by intranasal administration, by transmucosal administration, by rectal administration, and/or subcutaneous administration as well as intrathecal, intravenous, intramuscular, intraperitoneal, intranasal, intraocular and/or intraventricular injection. The compound or DNA-binding polymers of the instant invention can also be administered in a local rather than a systemic fashion, such as injection as a sustained release formulation. The following dosage forms are given by way of example and should not be construed as limiting the instant invention.

Compositions suitable for parenteral administration conveniently comprise a sterile aqueous preparation of the agent, which is preferably isotonic with the blood of the recipient. This aqueous preparation may be formulated according to known methods using suitable dispersing or wetting compounds and suspending compounds. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found, for example, in "Remington's Pharmaceutical Sciences" Mack Publishing Co., New Jersey (1991), which is incorporated herein by reference.

Preparations for parenteral administration include sterile aqueous or non-aqueous solutions, suspensions, and/or emulsions. Examples of non-aqueous solvents are propylene glycol, polyethylene glycol, vegetable oils such as olive oil, organic solvents such as dimethylacetamide and N-methylpyrrolidone, and/or injectable organic esters such as ethyl oleate. Aqueous carriers include water, alcoholic/aqueous solutions, emulsions or suspensions, including saline and/or buffered media. Parenteral vehicles include sodium chloride solution, Ringer's dextrose, dextrose and sodium chloride, lactated Ringer's and/or fixed oils. Intravenous vehicles include fluid and nutrient replenishers, and/or electrolyte replenishers (such as those based on Ringer's dextrose), and the like. Preservatives and other additives may also be present such as, for example, antimicrobials, anti-oxidants, chelating compounds, and inert gases and the like. The pharmaceutical compositions may conveniently be presented in unit dosage form and may be prepared by any of the methods well-known in the art of pharmacy.

Compositions suitable for oral administration may be presented as discrete units, such as capsules, tablets, and/or lozenges, each containing a predetermined amount of the agent. Other compositions include suspensions in aqueous liquids or non-aqueous liquids such as a syrup, elixir or an emulsion. Liquid dosage forms for oral administration may be in the form of pharmaceutically acceptable emulsions, syrups, elixirs, suspensions, slurries and/or solutions, which may contain an inactive diluent, such as water. Pharmaceutical formulations may be prepared as liquid suspensions or solutions using a sterile liquid, such as, but not limited to, an oil, water, and/or an alcohol, and combinations of these. Pharmaceutically suitable surfactants, suspending agents, and/or emulsifying agents, may be added for oral or parenteral administration.

Compositions may comprise a biocompatible microparticle or implant that is suitable for implantation. Biocompatible and biodegradable polymeric matrix materials may also be added. The polymeric matrix may be used to achieve sustained release of the agent in a subject. DNA-binding polymers of the invention may be encapsulated or dispersed within a biocompatible and biodegradable polymeric matrix. The polymeric matrix can be in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and/or stents. The size and composition of the polymeric matrix device is selected to result in favorable release kinetics in the tissue into which the matrix device is implanted. The size of the polymeric matrix device further is selected according to the method of delivery, which is to be used, typically injection into a tissue or administration of a suspension by aerosol into the nasal and/or pulmonary areas. The polymeric matrix composition can be selected to have both favorable degradation rates and also to be formed of a material, which is bioadhesive, to further increase the effectiveness of transfer when the device is administered to a vascular or pulmonary surface. The matrix composition also can be selected not to degrade, but rather, to release by diffusion over an extended period of time.

Both non-biodegradable and biodegradable polymeric matrices can be used to deliver the agents of the invention to the subject. Such polymers may be natural or synthetic polymers. Synthetic polymers are preferred. The polymer is selected based on the period of time over which release is desired, generally in the order of a few hours to a year or longer. The polymer optionally is in the form of a hydrogel that can absorb up to about 90% of its weight in water and further, optionally is cross-linked with multi-valent ions or other polymers.

Exemplary synthetic polymers which can be used include: polycarbonates, polyalkylenes, polyalkylene glycols, polyalkylene oxides, polyalkylene terpthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, and/or polystyrene, or combinations or mixtures thereof. Examples of non-biodegradable polymers include ethylene vinyl acetate, poly(meth)acrylic acid, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, and/or copolymers and mixtures thereof. In general, these materials degrade either by enzymatic hydrolysis or exposure to water in vivo, by surface or bulk erosion.

Bioadhesive polymers may also be included in the present compositions. Examples of such bioadhesive polymers include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and/or poly(octadecyl acrylate), or combinations or mixtures thereof.

Compositions of the present invention may be formulated as timed release, delayed release, or sustained release delivery systems. Such systems can avoid the need for repeated administrations of the agent of the invention, increasing convenience to the subject and the physician. Many types of release delivery systems are available and known to those of ordinary skill in the art. They include the above-described polymeric systems, as well as polymer base systems such as poly(lactide-glycolide), polyoxalates, polycaprolactones, polyesteramides, polyorthoesters, polyhydroxybutyric acid, and/or polyanhydrides. Microcapsules of the foregoing polymers containing drugs are described in, for example, U.S. Pat. No. 5,075,109, expressly incorporated herein by reference. Delivery systems also include non-polymer systems that are: lipids including sterols such as cholesterol, cholesterol esters and fatty acids or neutral fats such as mono- di- and tri-glycerides, and phospholipids; hydrogel release systems; silastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854,480, 5,133,974 and 5,407,686, each of which is expressly incorporated herein by reference. In addition, pump-based hardware delivery systems can be used, some of which are adapted for implantation.

Use of a long-term sustained release implant may be used in the treatment of chronic conditions, such as the suspected presence of dormant metastases. Long-term release, are used herein, means that the implant is constructed and arranged to deliver therapeutic levels of the active ingredient for at least 30 days, at least 60 days and more preferably for several months. Long-term sustained release implants are well-known to those of ordinary skill in the art and include some of the release systems described above.

For oral, buccal, and sublingual administration, powders, suspensions, granules, tablets, pills, capsules, gelcaps, and/or caplets are acceptable as solid dosage forms. These can be prepared, for example, by mixing one or more DNA-binding polymers of the instant invention, or pharmaceutically acceptable salts or tautomers thereof, with at least one additive or excipient such as a starch or other additive. Suitable additives or excipients are sucrose, lactose, cellulose, sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents, and/or perfuming agents. Additionally, dyestuffs or pigments may be added for identification. Tablets and pills may be further treated with suitable coating materials known in the art.

As noted above, suspensions may include oils. Such oils include, but are not limited to, peanut oil, sesame oil, cottonseed oil, corn oil, soy bean oil, and/or olive oil. Suspension preparations may also contain esters of fatty acids such as ethyl oleate, isopropyl myristate, fatty acid glycerides, phospholipids, and/or acetylated fatty acid glycerides. Suspension formulations may include alcohols, such as, but not limited to, ethanol, isopropyl alcohol, hexadecyl alcohol, glycerol and/or propylene glycol. Ethers, such as but not limited to, poly(ethyleneglycol), petroleum hydrocarbons such as mineral oil and/or petrolatum; and/or water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00133813, WO 91/97947, U.S. Pat. Nos. 6,180,603, and 5,624,898, each of which is herein expressly incorporated by reference. A propellant for an aerosol formulation may include compressed air, nitrogen, carbon dioxide, or a hydrocarbon based low boiling solvent. The compound or DNA-binding polymers of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or diluents include sterilized water, 5% dextrose in water, Ringer's solution, or an isotonic aqueous saline solution. For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more DNA-binding polymers of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, lecithins, methyl cellulose, hydroxypropyl cellulose and/or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Compositions of the present invention embrace pharmaceutically acceptable salts of combination drugs of the invention. Pharmaceutically acceptable salts include a salt with an inorganic base, organic base, inorganic acid, organic acid, or basic or acidic amino acid. As salts of inorganic bases, the invention includes, for example, salts of alkali metals (such as sodium or potassium) and/or alkaline earth metals (such as calcium and magnesium or aluminum, and/or ammonia). As salts of organic bases, the invention may include, for example, salts of trimethylamine, triethylamine, pyridine, picoline, ethanolamine, diethanolamine, triethanolamine, tromethamine, choline, and/or meglumine. As salts of inorganic acids, the instant invention may include, for example, salts of hydrochloric acid, hydroboric acid, nitric acid, sulfuric acid, and/or phosphoric acid. As salts of organic acids, the instant invention may include, for example, salts of formic acid, acetic acid, trifluoroacetic acid, fumaric acid, oxalic acid, tartaric acid, maleic acid, citric acid, succinic acid, malic acid, methanesulfonic acid, benzenesulfonic acid, and/or p-toluenesulfonic acid.

The present invention is further illustrated by the following examples, which are not intended to be limiting in any way whatsoever.

EXAMPLES

Example 1

1.1 Background

Prostate cancer is the second leading cause of cancer death in American men, accounting for 26,000 deaths per year (1). The majority of prostate cancer deaths are attributable to progression of treatment resistant metastatic disease. First line treatment for metastatic prostate cancer is androgen deprivation therapy (ADT), which interferes with Androgen Receptor (AR) driven transcription by lowering serum testosterone to castrate levels. Eventually, however, castration-resistance emerges, most commonly through up-regulation of AR mRNA, which renders AR less sensitive to therapies that directly or indirectly interfere with androgen-AR binding. However, second-line therapeutics that potently inhibit androgen-AR binding directly or indirectly retain activity in castrate resistant prostate cancer (CRPC). One such drug, enzalutamide, a potent AR-ligand binding domain antagonist that prevents AR nuclear translocation, improves overall survival in patients with metastatic CRPC (2). Unfortunately, most patients develop disease that is resistant to enzalutamide.

A number of mechanisms of resistance to enzalutamide have been identified (3). These include restoration of AR signaling through LBD mutations or expression of transcriptionally active splice variants lacking the LBD (4), bypass of AR signaling through alternative NHRs (5), or development of complete independence from AR signaling (6). GR is a NHR with a sequence preference similar to AR (7). After enzalutamide treatment, the LREX' cell line highly expresses GR, which drives enzalutamide resistance by regulating gene expression significantly overlapping that of AR, suggesting CaPs co-opt GR to progress through AR antagonism (5). Furthermore, GR expression in mCRPC associates with poor response to enzalutamide (5). Therefore, interference with the NHR-DNA interface may overcome enzalutamide resistance. Finally, a percentage of prostate cancers after long-term androgen suppression develop features of neuroendocrine differentiation reminiscent to those of small cell carcinoma, a highly treatment-refractory histologic subtype of prostate cancer. For these patients, treatment paradigms beyond hormone manipulation may be required. Therapeutics that can simultaneously target multiple cellular events required for tumor progression may offer a pathway forward for treatment refractory prostate cancer patients.

Abbreviations: AR, androgen receptor; ARE, androgen response element; PSA, prostate-specific antigen; DHT, dihydrotestosterone; LBD, ligand binding domain; CaP, cancer of the prostate.

1.2 Summary and Description

Figure 7A:
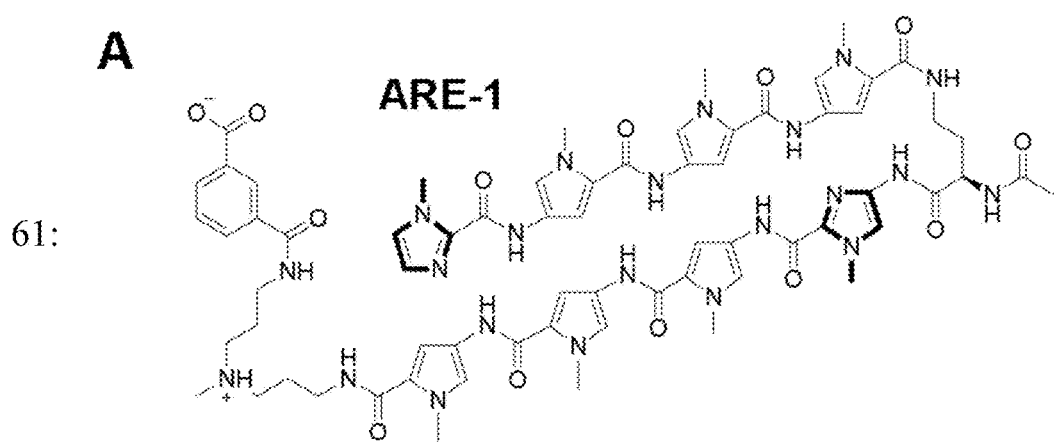
Figure 7B:
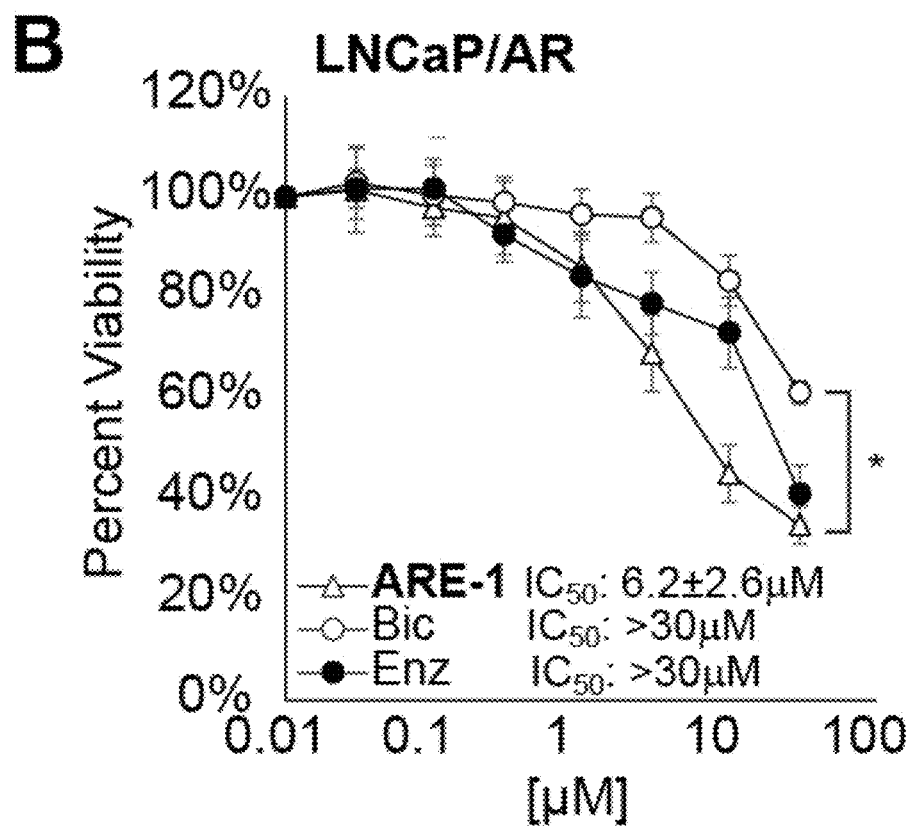
Figure 7C:
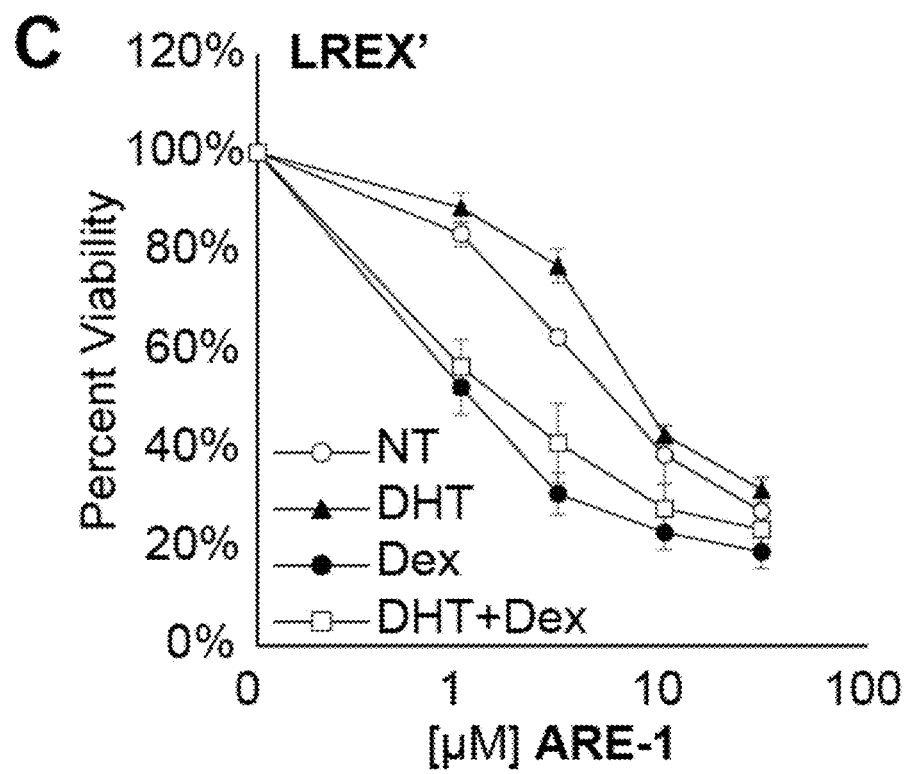
Figure 7D:
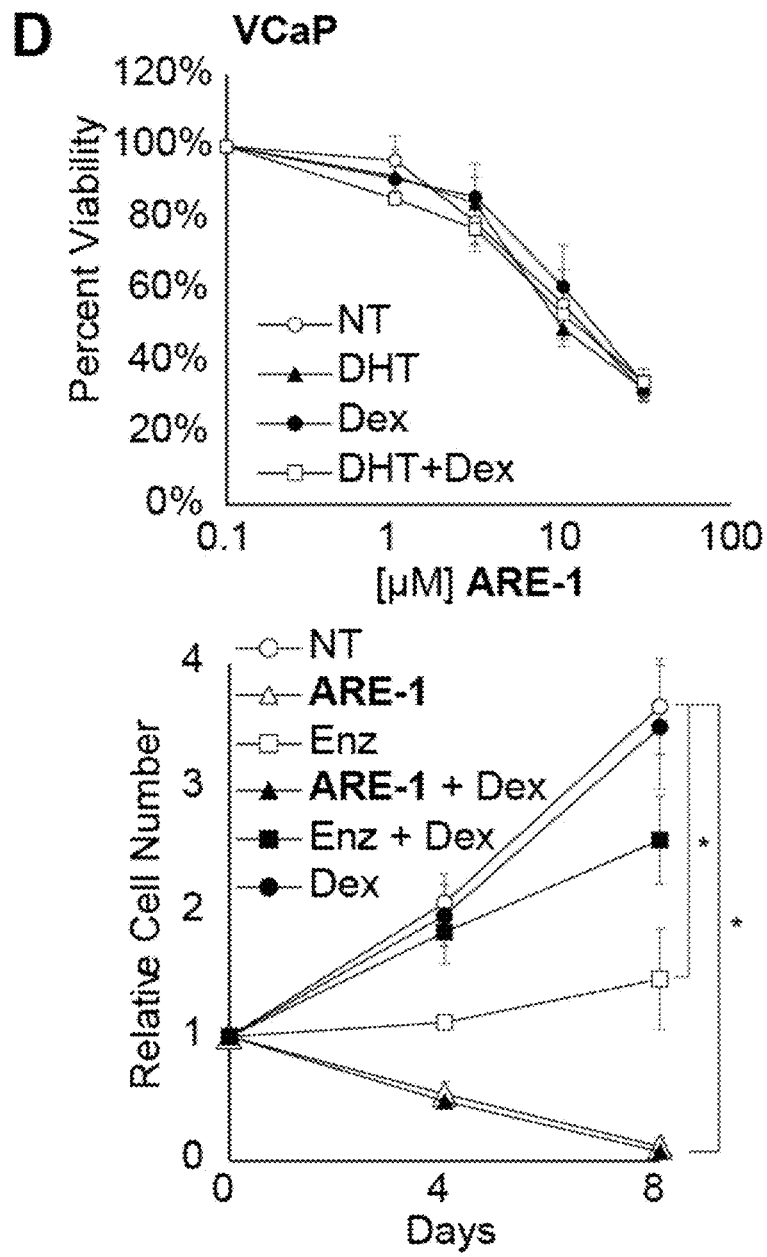

The following example demonstrates the development of a class of transcription inhibitors called pyrrole-imidazole (Py-Im) polyamides. Py-Im polyamides are minor groove DNA binding small molecules with modular sequence specificity and high affinity (9). Polyamide-DNA binding induces widening of the minor groove and compression of the opposing major groove (8), interfering with transcription factor-DNA interactions and the transcriptional machinery (10,11). A Py-Im polyamide was developed that is capable of blocking gene expression in prostate cancer cells (FIG. 7A) and causing cell death (FIG. 7B-7D). This molecule (ARE-1) was previously shown to effective against hormone sensitive LNCaP xenografts with minimal host toxicity (12). This example also demonstrates the combinatorial effects of compound ARE-1 with other agents used in prostate cancer therapy that have been shown to inhibit the androgen receptor signaling axis. While an additive reduction was seen for combination of ARE-1 with abiraterone, bicalutamide, docetaxel, and enzalutamide (FIG. 7E-7F), the effect was greatest for enzalutamide, an unexpected finding since both bicalutamide and enzalutamide are anti-androgens. Furthermore, an additive effect towards AR signaling antagonism was observed in LREX' cells cotreated with the Py-Im polyamide and the anti-androgen enzalutamide (FIG. 7B). These data provide compelling evidence that combination therapy with Py-Im polyamides and anti-androgen agents represent a viable therapeutic option for patients with metastatic castration-resistant prostate cancer.

1.3 Materials and Methods

1.3.1 Cell Culture Conditions and Cytotoxicity Assays

The LREX' and LNCaP/AR cell lines were gifts from Charles Sawyers (Memorial Sloan Kettering) and received in 2014 and 2007, respectively. The VCaP cell line was a gift from Kenneth Pienta (University of Michigan Medical School) and received in 2012. Cells were maintained as previously described (5, 10-13), and were used within 10 passages from thawing. Cells were validated to parental cell lines by STR profile at IDEXXX Bioresearch following experimentation and confirmed to be *Mycoplasma* free. WST-1 assay (Roche) was used to measure cytotoxicity. The CellTiter-Glo assay was also used in some experiments and is described when used. Long-term toxicity in VCaP cells was assayed by cell counting.

1.3.2 Confocal Imaging

Imaging was performed as previously described (12). Briefly, 2 µM of ARE-1-FITC was added for 16 hours, washed with PBS, and imaged on a Zeiss LSM 5 Exciter.

1.3.3 Gene Expression Analysis

LNCaP/AR and LREX' cells were cultured for 72 hours after plating in phenol-red free RPMI 1640 (10% CT-FBS) in six well plates at 40,000 and 50,000 cells/mL, respectively. LNCaP/AR cells were treated with 10 μM ARE-1, bicalutamide (bic), or enzalutamide (enz, Aurum Pharmatech) for an additional 48, 2, and 2 hours, respectively, prior to treatment with 1 nM DHT or ethanol for 16 hours. LREX' cells were treated with 10 μM ARE-1 for 16 hours prior to induction with 1 nM DHT or 100 nM dexamethasone (dex) for 8 hours. RNA extraction (RNEasy columns, Qiagen), cDNA generation (Transcriptor First Strand cDNA kit, Roche), and qRT-PCR (SYBR Green Master Mix, Applied Biosystems, ABI7300 instrument) were as described (10-12). Expression was normalized to β-glucuronidase.

1.3.4 RNAseq Analysis

LREX' cells were plated at 50,000 cells/mL in 10 cm$^2$ dishes, treated with or without 10 μM of ARE-1 in fresh media, incubated 16 hours, and induced with 1 nM DHT for 8 hours. Tumor samples were homogenized mechanically. Total RNA was triazol extracted, sequenced (Illumina HiSeq2000), mapped against the human genome (hg19) with Tophat2 using Ensembl GRCh37 gene annotations. Human and mouse reads from tumor samples were parsed with BBSplit and unique reads were mapped. Htseq-count was used for exon alignment and DESeq2 for differential expression. Gene set enrichment analysis (GSEA) was performed on genes with padj<0.05 and fold change≥1.6 for cell samples and padj<0.05 for tumor samples.

1.3.5 Nascent RNA Measurement

LREX' cells were plated at 100,000 cells/mL in 96 well plates in RPMI 1640 (20% FBS and 1 μM enz), adhered for 24 hours, dosed with ARE-1, incubated for 48 hours. The Click-iT® RNA Alexa Fluor® 488 HCS kit was used for dye conjugation and incorporation of 5-ethynyl uridine (5-EU) was measured on a Flexstation 3 plate reader.

1.3.6 Flow Cytometry

LREX' cells were plated at 100,000 cells/mL in 175 cm$^2$ flasks, adhered 24 hours, incubated with 10 μM ARE-1 24, 48, and 72 hours, then with 300 μM 5-EU in fresh media. Cells were detached by Accumax or Accutase, and Alexa Fluor® 488 azide dye was conjugated. Cells were passed through 35 μm mesh prior to flow, sorted on a FACSCalibur instrument (Beckman-Dickinson), analyzed using FlowJo.

1.3.7 Animal Experiments

Animal experiments were performed at Caltech under IACUC approval. VCaP and LREX' cells were engrafted as 1:1 mixtures of 3×10$^6$ cells in Matrigel (BD Biosciences) into flanks of intact and castrated male SCID mice (Charles River), respectively. LREX' engrafted mice received 10 mg/kg enz (oral gavage) daily. Once tumors were 100 mm$^3$ (0.5*l*w*w), ARE-1 was administered subcutaneously to opposing flanks in 20% DMSO:saline. For circulation studies, four C57BL6/J animals were injected subcutaneously with ARE-1 at 30 mg/kg and blood collected retroorbitally. Plasma concentrations of ARE-1 were analyzed by HPLC, area under the curve (AUC) approximated by the linear trapezoidal method, as described (12).

1.3.8 Immunohistochemistry

Tumors were fixed in neutral-buffered formalin, paraffinized, sectioned, stained as described (11). Quantification of five random fields per slice was performed by ImmunoRatio.

1.3.9 Statistical Analysis

Cell culture experiments represent ≥3 independent biological replicates. Sequencing analyses were duplicates for cell culture and quadruplicates for tumor samples. For xenografts, animals were randomly assigned to groups. For circulation experiments, concentrations of ARE-1 were duplicate measurements. Measurements in cell culture, animal, and immunohistochemistry experiments were assessed by Student's t-test.

1.4 Results

Figure 7E:
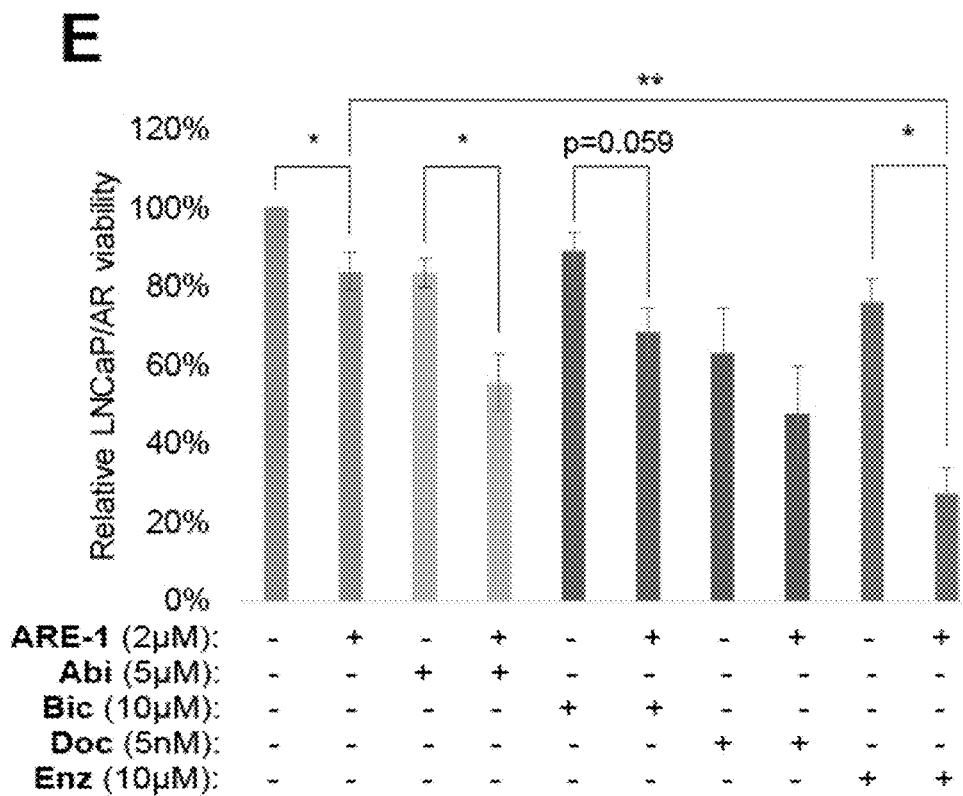
Figure 7F:
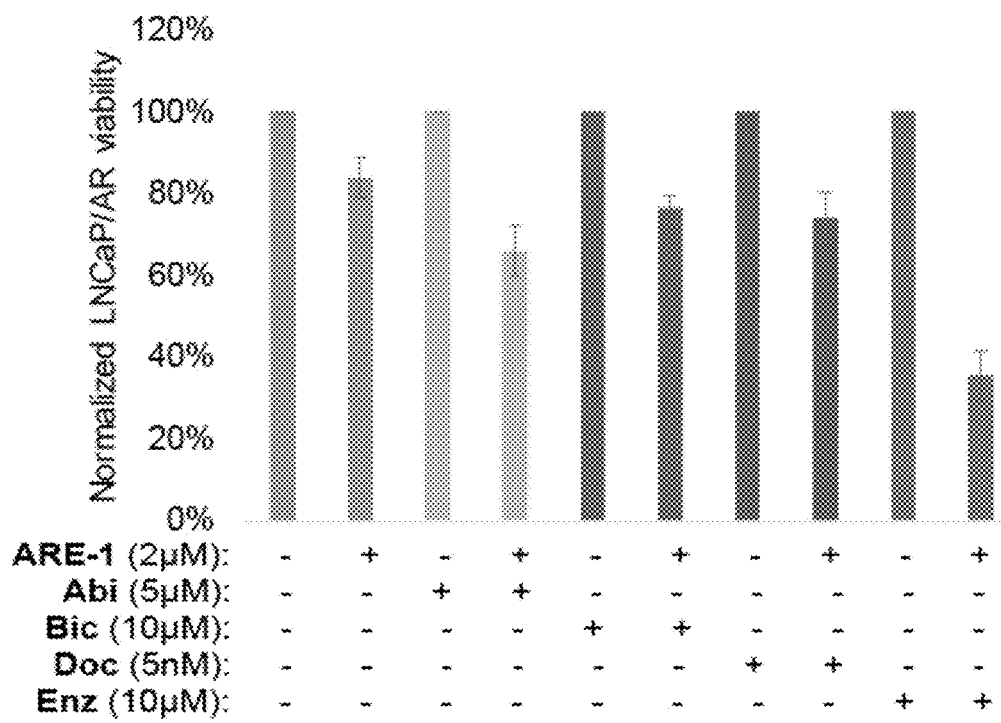

1.4.1 ARE-1 is More Potent than Enzalutamide Against CaP Cell Growth and is not Rescued by GR Activation ARE-1 (FIG. 7A) targets the sequence 5'-WGWWCW-3' (W=A or T), similar to the consensus half site recognized by either AR or GR. Nuclear uptake in LNCaP/AR, LREX', and VCAP cells was evaluated using fluorescent analog ARE-1-FITC (FIG. 8A-8B). The LNCaP/AR cell line overexpresses full length AR, modeling castration resistance (14). ARE-1 reduced proliferation of LNCaP/AR cells more than bicalutamide (FIG. 7B). The VCaP cell line overexpresses AR with modest GR expression, the activation of which reduces the antiproliferative effects of enzalutamide (5). ARE-1 reduced proliferation of both VCaP and LREX' cells regardless of induction of AR signaling by 1 nM DHT, induction of GR signaling by 100 nM dex, or both (FIG. 7C-7D). Long-term cell viability studies in VCaP cells show ARE-1 is more potent than enzalutamide and insensitive to GR activation (FIG. 7D). The combinatorial effect of ARE-1 was investigated with therapeutics used in prostate cancer treatment that antagonize AR signaling. In LNCaP/AR cells, combinations of ARE-1 with abiraterone, bicalutamide, docetaxel, and enzalutamide showed additive effects towards growth inhibition (FIG. 7E-7F). Surprisingly, ARE-1 with enzalutamide exhibited the greatest growth inhibition.

Figure 9A:
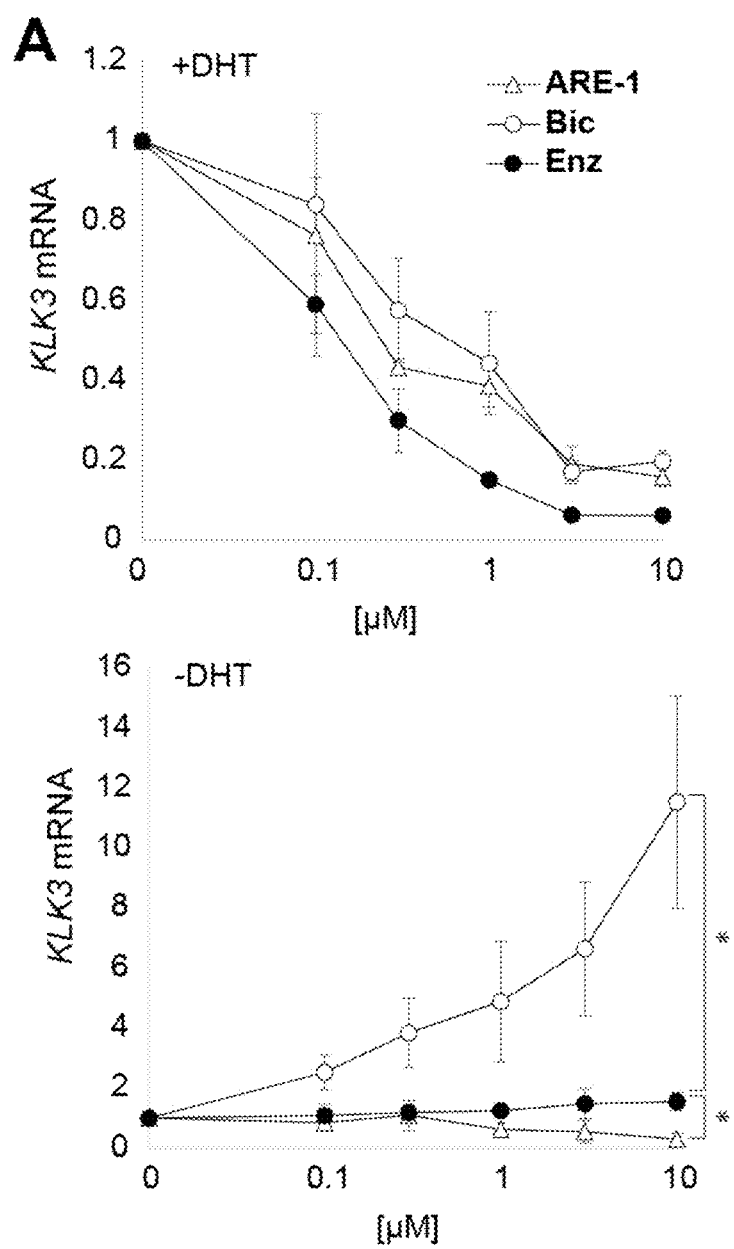
Figure 9B:
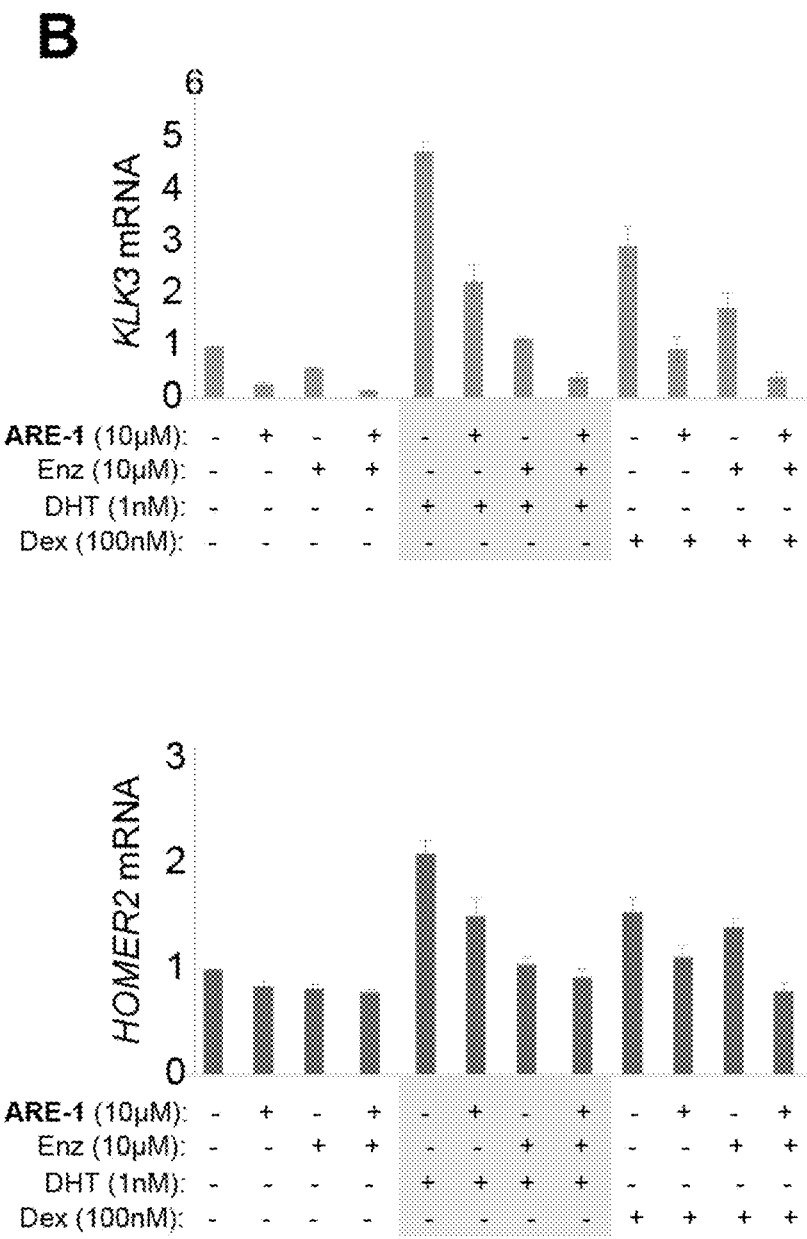

1.4.2 Py-Im Polyamide Attenuates Androgen and Glucocorticoid Driven Gene Expression In androgen-depleted conditions, bicalutamide activates AR in the LNCaP/AR cell line (14). Enzalutamide and ARE-1 demonstrate no agonist activity; ARE-1 reduced baseline expression of KLK3 (FIG. 9A). In LREX' cells, ARE-1 represses KLK3 and HOMER2 expression, which are co-regulated by AR and GR (FIG. 9B). While enzalutamide was more potent than ARE-1 in reducing DHT induced transcription, the opposite was observed with dex induction. Furthermore, co-administration of enzalutamide and ARE-1 was additive, suggesting ARE-1 may potentiate enzalutamide's activity.

1.4.3 Global Transcriptomic Effects of Py-Im Polyamides

Figure 9C:
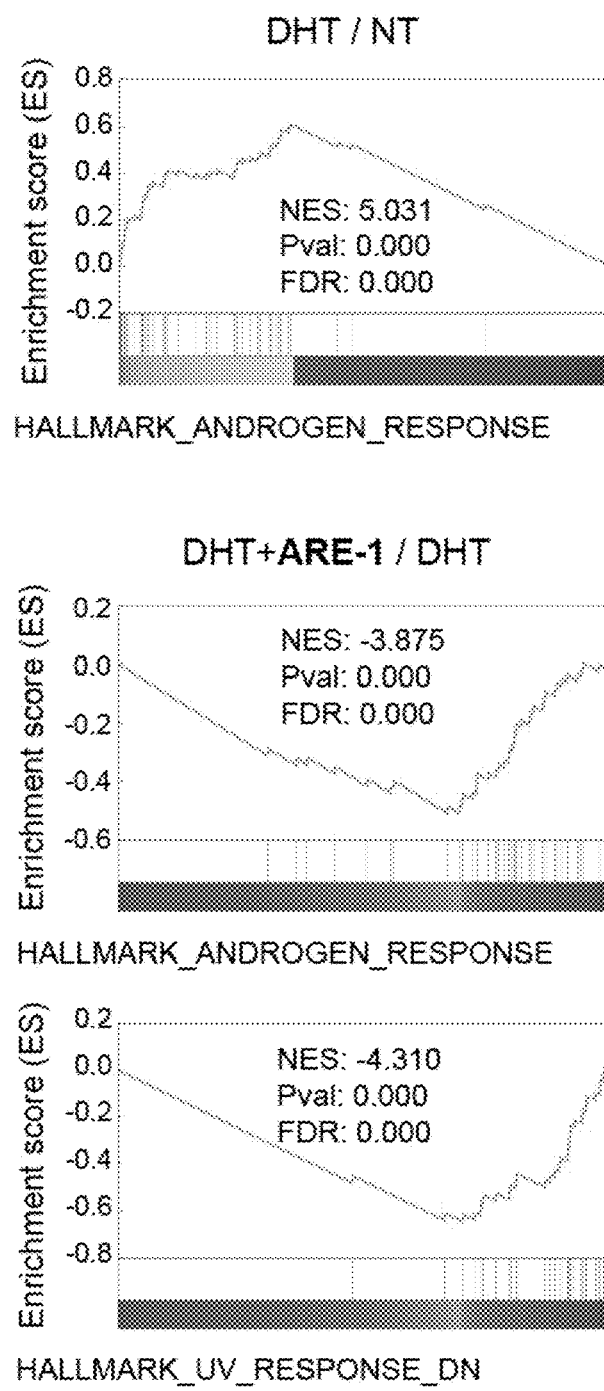
Figure 9D:
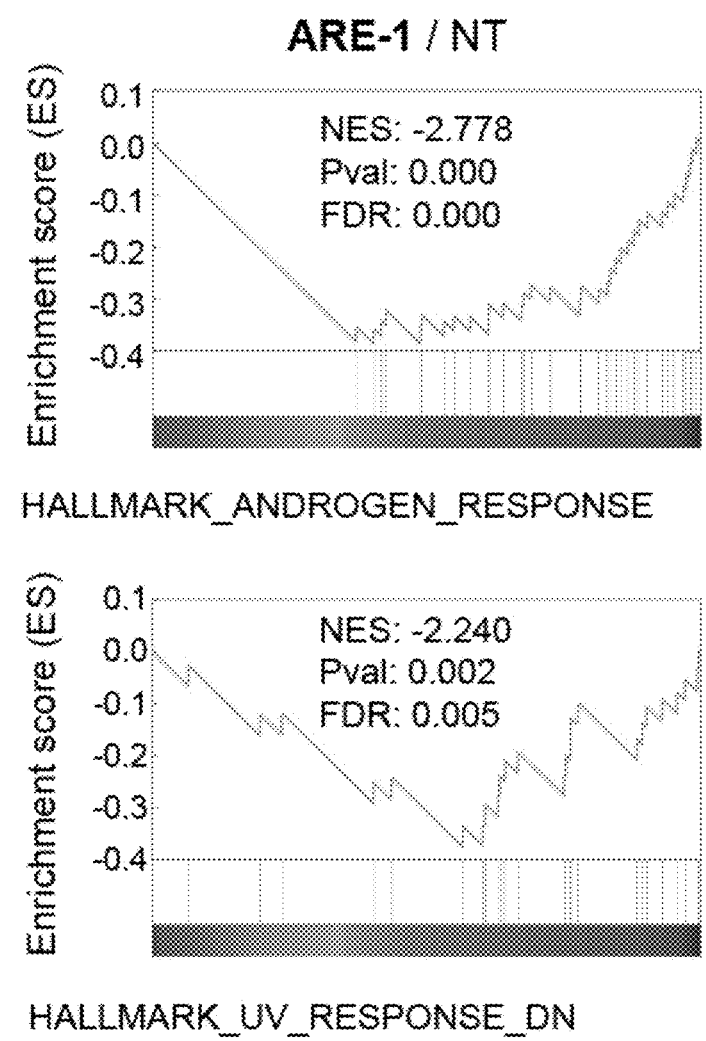

RNA-seq analysis was performed on three treatment conditions in LREX' cells: vehicle, DHT treatment, and co-treatment with ARE-1 and DHT, and two conditions in parental LNCaP cells: vehicle, and ARE-1 treatment. GSEA of affected genes in LREX' cells using the hallmark pathways in the Molecular Signatures Database revealed DHT treatment enriched for the AR signaling pathway as expected (FIG. 9C, FIG. 10 and Table 1). DHT-induced LREX' cells treated with ARE-1 negatively enriched for the AR signaling pathway (NES −3.875) (FIG. 9C, Table 1), consistent with interference in AR-driven gene expression by ARE-1. Additionally, ARE-1 treatment negatively enriched for the UV DNA damage response pathway down (NES −4.310) (FIG. 9C). Similarly, ARE-1 treatment in LNCaP cells negatively enriched for the AR signaling pathway (NES −2.778) and the UV DNA damage response pathway down (NES −2.240) (FIG. 9D, Table 1). UV radiation induces DNA helical distortions through formation of pyrimidine dimers and 6-4 photoproducts, which arrest RNA Polymerase II (RNAP2) during elongation, triggering degradation of RPB1. ARE-1 reduced nascent RNA in LREX' cells as measured by 5-EU incorporation (FIG. 11A-11C). Previous observations showed RPB1 degradation after long-term treatment with ARE-1 and related polyamides (11,12). This suggests long-term treatment with ARE-1 reduces global transcription in LREX' cells.

TABLE 1

Table 1: GSEA of DHT/NT and DHT + ARE-1/DHT condition in LREX' cells, and ARE-1/NT in LNCaP cells. Top 5 positively and negatively enriched Hallmark pathways with FDR <0.05 are listed.

| Enrichment Terms | NES | Pval | FDR |
|---|---|---|---|
| Condition: LREX' DHT/NT | | | |
| HALLMARK ANDROGEN RESPONSE | 5.0307606 | 0 | 0 |
| HALLMARK PROTEIN SECRETION | 2.8486454 | 0 | 0 |
| HALLMARK TNFA SIGNALING VIA NFKB | 2.7508241 | 0 | 0 |
| HALLMARK UV RESPONSE DOWN | 2.4962228 | 0 | 0.0010452 |
| HALLMARK MYC TARGETS V2 | -1.810043 | 0.018797 | 0.0436006 |
| HALLMARK MYC TARGETS V1 | -1.8610797 | 0.0056497 | 0.0482218 |
| HALLMARK OXIDATIVE PHOSPHORYLATION | -2.1263347 | 0.0058594 | 0.0168776 |
| Condition: LREX' DHT + ARE-1/DHT | | | |
| HALLMARK OXIDATIVE PHOSPHORYLATION | 2.738261 | 0 | 0.0010684 |
| HALLMARK UV RESPONSE UP | 2.1734213 | 0.0020284 | 0.0192308 |
| HALLMARK DNA REPAIR | 2.0550299 | 0.0019608 | 0.0281339 |
| HALLMARK INTERFERON GAMMA RESPONSE | 2.0279558 | 0.004065 | 0.0224359 |
| HALLMARK MYC TARGETS V1 | 2.0058489 | 0.0019763 | 0.0194444 |
| HALLMARK APICAL JUNCTION | -2.1975774 | 0 | 0.005597 |
| HALLMARK MITOTIC SPINDLE | -2.3021617 | 0 | 0.0037313 |
| HALLMARK PROTEIN SECRETION | -2.4021989 | 0 | 0.0031095 |
| HALLMARK ANDROGEN RESPONSE | -3.8752934 | 0 | 0 |
| HALLMARK UV RESPONSE DOWN | -4.3098002 | 0 | 0 |
| Condition: LNCaP ARE-1/NT | | | |
| HALLMARK P53 PATHWAY | 3.7487608 | 0 | 0 |
| HALLMARK TNFA SIGNALING VIA NFKB | 3.2482756 | 0 | 0 |
| HALLMARK INTERFERON GAMMA RESPONSE | 3.0602648 | 0 | 0 |
| HALLMARK APOPTOSIS | 2.3234139 | 0.0019194 | 0.0005936 |
| HALLMARK UV RESPONSE DOWN | -2.2403436 | 0.0017953 | 0.0048524 |
| HALLMARK ANDROGEN RESPONSE | -2.7783908 | 0 | 0 |

Figure 13A:
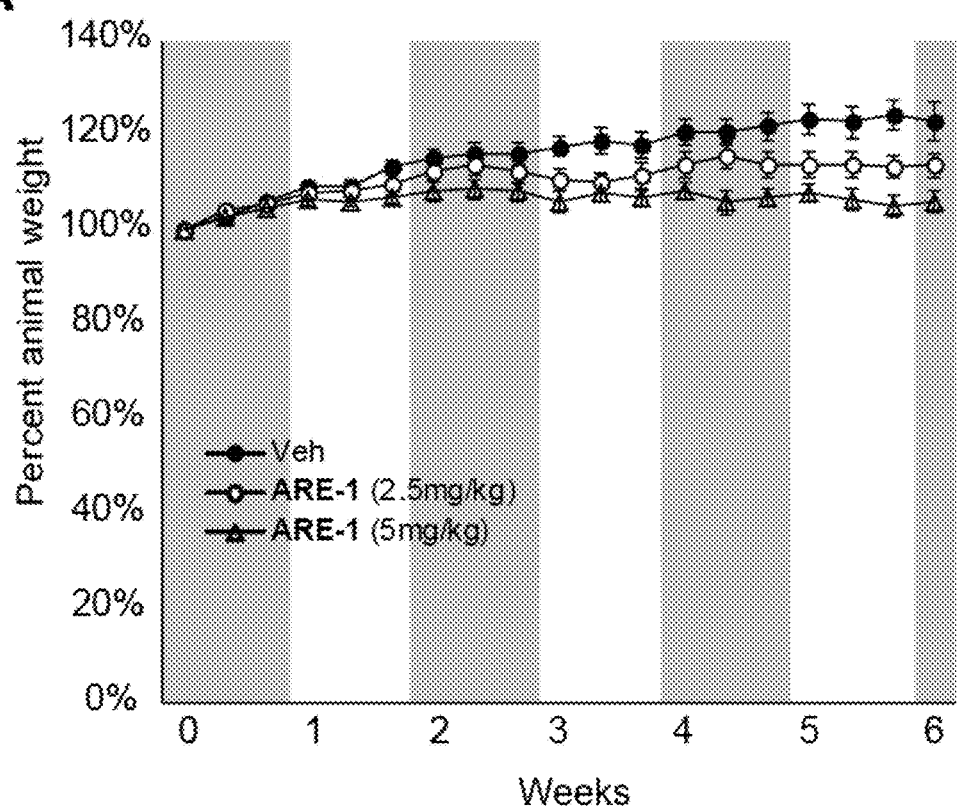
Figure 13B:
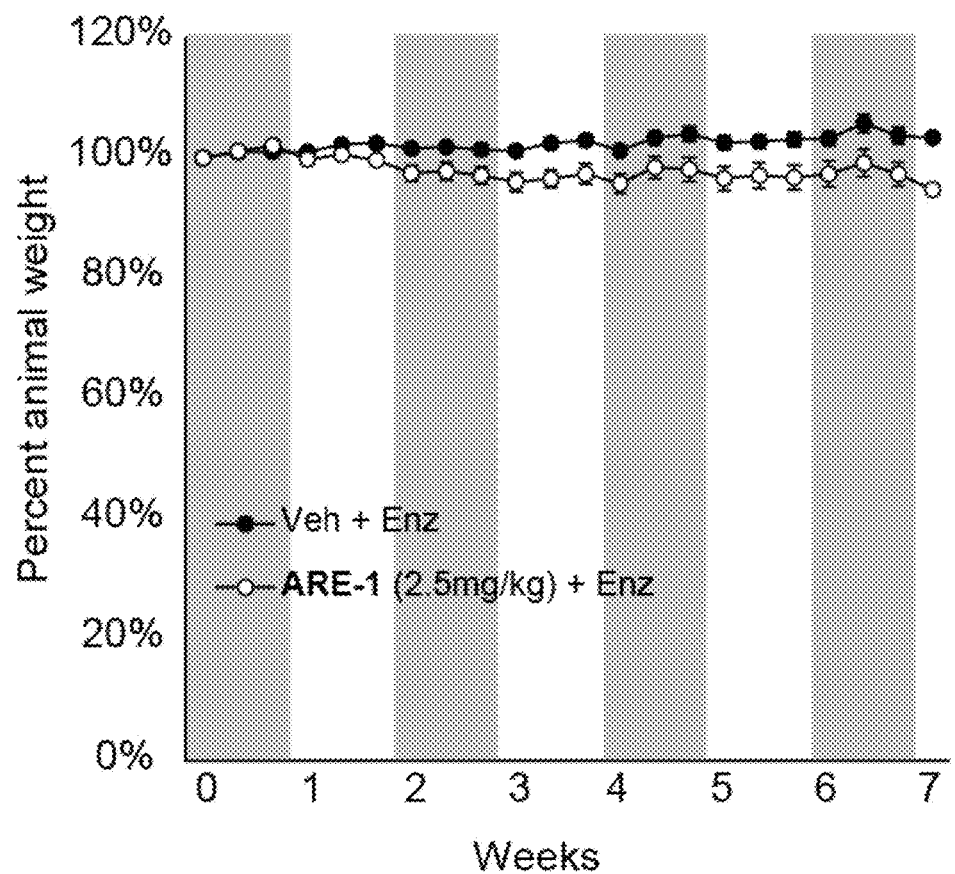
Figure 13C:
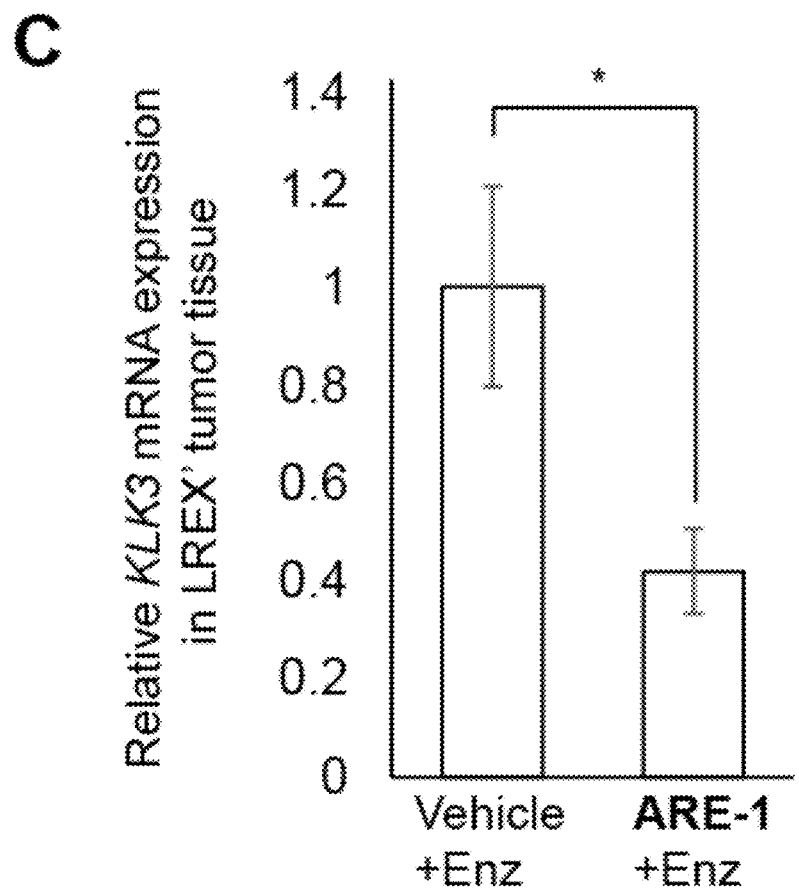
Figure 13D:
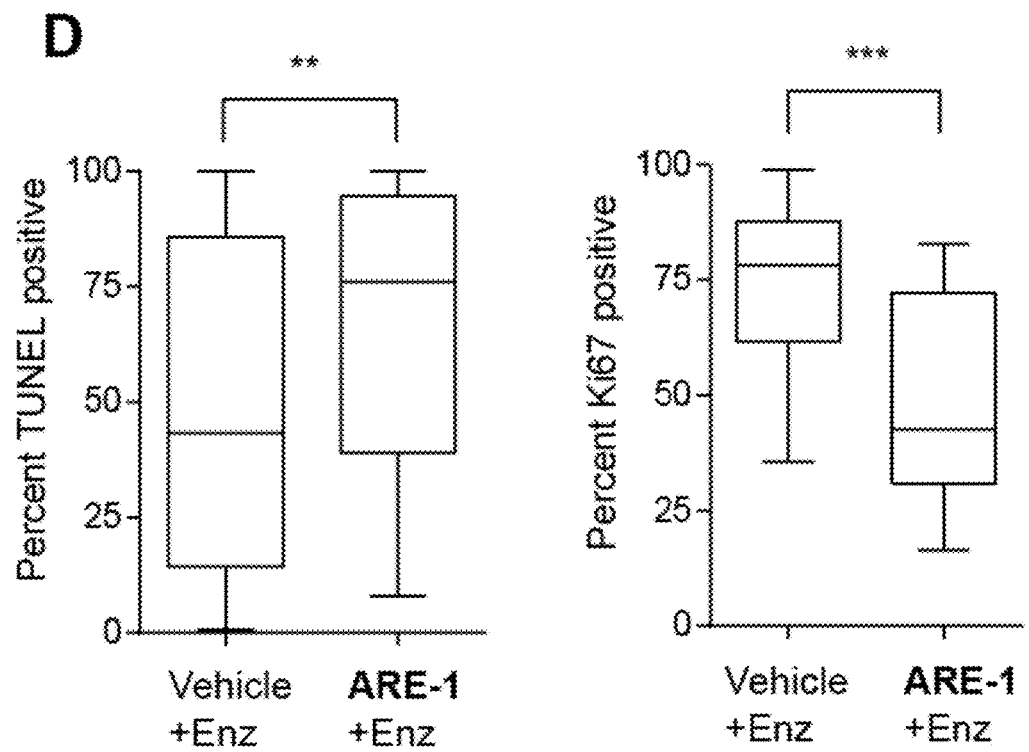

1.4.4 Suppression of Enzalutamide Resistant, Castrate Resistant CaP In Vivo ARE-1 efficacy was tested in VCaP xenografts, which exhibits a modest response to 10 mg/kg enzalutamide treatment, and in mice engrafted with enzalutamide resistant LREX' cells (5,13). In VCaP xenografts, ARE-1 dose-dependently reduced tumor growth by 70% at 5 mg/kg compared to vehicle (FIG. 12A) without significant toxicity (FIG. 13A). In castrated mice bearing LREX' tumors, ARE-1 and enzalutamide cotreatment reduced growth by 80% compared to enzalutamide alone (FIG. 12B) without significant toxicity (FIG. 13B). Enzalutamide was administered daily post engraftment at 10 mg/kg to maintain GR expression, which was confirmed by immunohistochemistry. LNCaP tumors, which do not express GR, were used as controls (FIG. 12C). Furthermore, LREX' tumors treated with ARE-1 and enzalutamide showed reduced KLK3 expression (FIG. 13C), elevated TUNEL and reduced Ki67 staining compared to enzalutamide alone (FIG. 13D). GSEA of tumor expression profiles show ARE-1 treatment elicits similar UV response signatures as seen in cell culture, and represses ontologies associated with DNA binding dependent transcription (Tables 2 and 3). Plasma concentration of ARE-1 from terminal blood samples from LREX' engrafted animals was compared to the plasma concentration in C57BL6/J animals treated with 30 mg/kg; AUC was 25.9 and 189.9 µg*hr/mL, respectively (FIG. 14). At 30 mg/kg mice experienced a 6% weight loss but recovered within 5 days without visible signs of distress (not shown).

TABLE 2

Table 2: GSEA of Enz+ARE-1/Enz+vehicle expression profiles of LREX' tumors. Top 5 positively and negatively Hallmark pathways with FDR <0.05 are listed.

| Enrichment Terms | NES | Pval | FDR |
|---|---|---|---|
| HALLMARK OXIDATIVE PHOSPHORYLATION | 3.8754299 | 0 | 0 |
| HALLMARK MYC TARGETS V1 | 2.7354496 | 0 | 0 |
| HALLMARK DNA REPAIR | 2.254965 | 0.0019685 | 0.0081733 |
| HALLMARK XENOBIOTIC METABOLISM | 1.9715754 | 0.0039761 | 0.0360503 |
| HALLMARK FATTY ACID METABOLISM | 1.915122 | 0.0059642 | 0.0395982 |
| HALLMARK G2M CHECKPOINT | -1.9537216 | 0.0099206 | 0.0218211 |
| HALLMARK UV RESPONSE DOWN | -2.3472996 | 0 | 0.0023326 |
| HALLMARK HYPOXIA | -2.4245274 | 0 | 0.0018768 |
| HALLMARK MITOTIC SPINDLE | -4.0181766 | 0 | 0 |

TABLE 3

Table 3: GSEA of gene ontology of LREX' tumor expression profiles.

| Gene Ontology Term | Nes | Pval | FDR |
|---|---|---|---|
| MITOCHONDRION | 6.584773 | 0 | 0 |
| ORGANONITROGEN COMPOUND METABOLIC PROCESS | 5.958487 | 0 | 0 |
| MITOCHONDRIAL PART | 5.946175 | 0 | 0 |
| MITOCHONDRIAL ENVELOPE | 5.169817 | 0 | 0 |
| ORGANELLE INNER MEMBRANE | 4.9216123 | 0 | 0 |
| ORGANONITROGEN COMPOUND BIOSYNTHETIC PROCESS | 4.8149147 | 0 | 0 |
| RIBOSOME | 4.7787743 | 0 | 0 |
| STRUCTURAL CONSTITUENT OF RIBOSOME | 4.7411127 | 0 | 0 |
| CELLULAR AMIDE METABOLIC PROCESS | 4.7254405 | 0 | 0 |
| MITOCHONDRION ORGANIZATION | 4.686384 | 0 | 0 |
| MACROMOLECULAR COMPLEX BINDING | -3.7259953 | 0 | 0 |
| CHROMATIN BINDING | -3.7858937 | 0 | 0 |
| CELL PROJECTION ORGANIZATION | -3.8129647 | 0 | 0 |
| ZINC ION BINDING | -3.9227276 | 0 | 0 |
| DOUBLE STRANDED DNA BINDING | -4.0743546 | 0 | 0 |
| ADENYL NUCLEOTIDE BINDING | -4.2202587 | 0 | 0 |
| REGULATION OF TRANSCRIPTION FROM RNA POLYMERASE II PROMOTER | -4.437626 | 0 | 0 |
| REGULATORY REGION NUCLEIC ACID BINDING | -4.775455 | 0 | 0 |

TABLE 3-continued

Table 3: GSEA of gene ontology of LREX' tumor expression profiles.

| Gene Ontology Term | Nes | Pval | FDR |
|---|---|---|---|
| SEQUENCE SPECIFIC DNA BINDING | −4.9900775 | 0 | 0 |
| NUCLEIC ACID BINDING TRANSCRIPTION FACTOR ACTIVITY | −5.598217 | 0 | 0 |

1.5 Discussion

AR LBD mutations, expression of transcriptionally active splice variants lacking the LBD, co-option of NHRs with similar DNA binding specificities, or loss of reliance on AR, may drive enzalutamide resistance (3). Furthermore, different metastatic foci within a patient may resist enzalutamide through different mechanisms (15), suggesting a successful treatment strategy might use multiple therapeutics that overcome different resistance mechanisms, or alternatively, a single therapeutic capable of overcoming multiple mechanisms. Therapeutic targeting of the NHR-DNA interface may overcome most known enzalutamide resistance mechanisms.

The GR antagonist mifepristone added to ADT was previously tested in mCRPC patients and was not effective (16). Trials for mCRPC patients combining enzalutamide with mifepristone are underway. Other NHRs may also be active in refractory CaP (3). Notably, progesterone receptor inhibitors have entered clinical trials for mCRPC. Therapeutics targeting the N-terminal domain (NTD) of AR, or that mediate degradation of AR, may overcome treatment resistance due to AR splice variants. The NTD inhibitor EPI-506 has entered clinical trials (17). However, this approach may not overcome resistance due to co-option of alternate NHRs. Others have reported small molecules that interfere with the AR DNA-binding domain (18). The clinical utility of this approach is unknown.

The disclosed Py-Im polyamide shows activity against enzalutamide-resistant CaP in cell and animal models. Polyamide ARE-1, targeted to the sequence 5'-WGWWCW-3', which is similar to the ARE and GRE half site, attenuates ligand induced AR and GR transcriptional activity, is more potent than enzalutamide and bicalutamide in cell culture, and is active against enzalutamide resistant xenografts. Long term treatment of LREX' cells with ARE-1 also decreases nascent RNA synthesis. In biophysical experiments, polyamides can halt RNAP2 elongation directly upstream of a polyamide binding site (19). Without wishing to be bound by theory, the stalling of RNAP2 may promote ubiquitination and degradation of RPB1, ultimately interfering with RNA synthesis, which may contribute to efficacy against treatment refractory CaP. Other molecules that interfere with RNA synthesis are proposed as potential drug candidates for CaP (13,20).

REFERENCES FOR EXAMPLE 1

The following citations (and any citation in the present specification) are each expressly incorporated by reference in its entirety.

1. American Cancer Society. Cancer Facts & FIGS. 2016. Atlanta: American Cancer Society; 2016.
2. Beer T M, Armstrong A J, Rathkopf D E, Loriot Y, Sternberg C N, Higano C S, et al. Enzalutamide in Metastatic Prostate Cancer before Chemotherapy. N Engl J Med. 2014; 371:424-33.
3. Watson P A, Arora V K, Sawyers C L Emerging mechanisms of resistance to androgen receptor inhibitors in prostate cancer. Nat Rev Cancer. 2015; 15:701-11.
4. Ware K E, Garcia-Blanco M A, Armstrong A J, Dehm S M. Biologic and clinical significance of androgen receptor variants in castration resistant prostate cancer. Endocr Relat Cancer. 2014; 21:T87-103.
5. Arora V K, Schenkein E, Murali R, Subudhi S K, Wongvipat J, Balbas M D, et al. Glucocorticoid Receptor Confers Resistance to Antiandrogens by Bypassing Androgen Receptor Blockade. Cell. 2013; 155:1309-22.
6. Beltran H, Prandi D, Mosquera J M, Benelli M, Puca L, Cyrta J, et al. Divergent clonal evolution of castration-resistant neuroendocrine prostate cancer. Nat Med. 2016; 22:298-305.
7. Meijsing S H, Pufall M A, So A Y, Bates D L, Chen L, Yamamoto K R. DNA binding site sequence directs glucocorticoid receptor structure and activity. Science. 2009; 324:407-10.
8. Chenoweth D M, Dervan P B. Allosteric modulation of DNA by small molecules. Proc Natl Acad Sci USA. 2009; 106:13175-9.
9. Dervan P B, Edelson B S. Recognition of the DNA minor groove by pyrrole-imidazole polyamides. Curr Opin Struct Biol. 2003; 13:284-99.
10. Nickols N G, Dervan P B. Suppression of androgen receptor-mediated gene expression by a sequence-specific DNA-binding polyamide. Proc Natl Acad Sci USA. 2007; 104: 10418-23.
11. Yang F, Nickols N G, Li B C, Marinov G K, Said J W, Dervan P B. Antitumor activity of a pyrrole-imidazole polyamide. Proc Natl Acad Sci USA. 2013; 110:1863-8.
12. Yang F, Nickols N G, Li B C, Szablowski J O, Hamilton S R, Meier J L, et al. Animal toxicity of hairpin pyrrole-imidazole polyamides varies with the turn unit. J Med Chem. 2013; 56:7449-57.
13. Asangani I A, Dommeti V L, Wang X, Malik R, Cieslik M, Yang R, et al. Therapeutic targeting of BET bromodomain proteins in castration-resistant prostate cancer. Nature. 2014; 510:278-82.
14. Chen C D, Welsbie D S, Tran C, Baek S H, Chen R, Vessella R, et al. Molecular determinants of resistance to antiandrogen therapy. Nat Med. 2004; 10:33-9.
15. Gundem G, Van Loo P, Kremeyer B, Alexandrov L B, Tubio J M C, Papaemmanuil E, et al. The evolutionary history of lethal metastatic prostate cancer. Nature. 2015; 520:353-7.
16. Taplin M-E, Manola J, Oh W K, Kantoff P W, Bubley G J, Smith M, et al. A phase II study of mifepristone (RU-486) in castration-resistant prostate cancer, with a correlative assessment of androgen-related hormones. BJU Int. 2008; 101:1084-9.

17. Myung J-K, Banuelos C A, Fernandez J G, Mawji N R, Wang J, Tien A H, et al. An androgen receptor N-terminal domain antagonist for treating prostate cancer. J Clin Invest. 2013; 123:2948-60.

18. Dalal K, Roshan-Moniri M, Sharma A, Li H, Ban F, Hassona M D, et al. Selectively targeting the DNA-binding domain of the androgen receptor as a prospective therapy for prostate cancer. J Biol Chem. 2014; 289: 26417-29.

19. Xu L, Wang W, Gotte D, Yang F, Hare A A, Welch T R, et al. RNA polymerase II senses obstruction in the DNA minor groove via a conserved sensor motif. Proc Natl Acad Sci. 2016; 113:12426-31.

20. Peltonen K, Colis L, Liu H, Jiaamaa S, Zhang Z, Af Hällström T, et al. Small molecule BMH-compounds that inhibit RNA polymerase I and cause nucleolar stress. Mol Cancer Ther. 2014; 13:2537-46.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All publications, including patent documents and scientific articles, referred to in this application and the bibliography and attachments are incorporated by reference in their entirety for all purposes to the same extent as if each individual publication were individually incorporated by reference. The article "a" as used herein means one or more unless indicated otherwise. All headings are for the convenience of the reader and should not be used to limit the meaning of the text that follows the heading, unless so specified.

What is claimed is:

1. A combination drug that inhibits the growth of a prostate cancer cell, wherein the combination drug comprises a polyamide and a prostate agent, wherein the polyamide has structure 61 as follows:

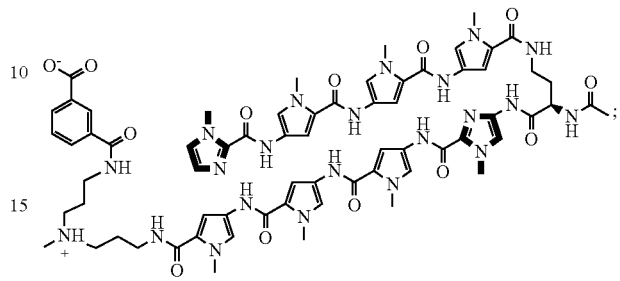

and wherein the prostate agent is enzalutamide.

2. The combination drug of claim 1, wherein said combination drug further comprises a pharmaceutically acceptable carrier.

3. The combination drug of claim 1, wherein said combination drug is formulated for parenteral administration.

4. The combination drug of claim 1, wherein the combination drug is formulated for subcutaneous administration.

5. The combination drug of claim 1, wherein the polyamide and the prostate agent comprise a single formulation.

6. The combination drug of claim 1, wherein the polyamide and the prostate agent comprise a single dosage.

7. The combination drug of claim 1, wherein the polyamide and the prostate agent are prepared as one preparation.

8. The combination drug of claim 1, wherein the polyamide and the prostate agent are prepared as two preparations.

9. The combination drug of claim 8, wherein the polyamide and the prostate agent are prepared as two preparations and wherein one preparation comprises the polyamide and the other preparation comprises the prostate agent.

* * * * *